(12) United States Patent
Buckanovich

(10) Patent No.: US 9,850,300 B2
(45) Date of Patent: Dec. 26, 2017

(54) COMPOSITIONS AND METHODS RELATING TO INHIBITING CANCER CELL GROWTH AND/OR PROLIFERATION

(71) Applicant: The Regents of the University of Michigan, Ann Arbor, MI (US)

(72) Inventor: Ronald Buckanovich, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/777,338

(22) PCT Filed: Mar. 12, 2014

(86) PCT No.: PCT/US2014/024070
§ 371 (c)(1),
(2) Date: Sep. 15, 2015

(87) PCT Pub. No.: WO2014/150720
PCT Pub. Date: Sep. 25, 2014

(65) Prior Publication Data
US 2016/0053006 A1  Feb. 25, 2016

Related U.S. Application Data

(60) Provisional application No. 61/790,138, filed on Mar. 15, 2013.

(51) Int. Cl.
*C07K 16/22* (2006.01)
*A61K 39/395* (2006.01)
*A61K 39/00* (2006.01)
*A61K 45/06* (2006.01)
*G01N 33/574* (2006.01)

(52) U.S. Cl.
CPC ........ *C07K 16/22* (2013.01); *A61K 39/39558* (2013.01); *A61K 45/06* (2013.01); *G01N 33/57449* (2013.01); *A61K 2039/505* (2013.01); *C07K 2317/34* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,876,973 A | 3/1999 | Marchionni | |
| 6,852,318 B1* | 2/2005 | Varner | A61K 38/08 424/130.1 |
| 2003/0166909 A1* | 9/2003 | Ford | C07K 14/71 536/23.5 |
| 2004/0059098 A1 | 3/2004 | Tang | |
| 2004/0197328 A1* | 10/2004 | Young | A61K 47/48569 424/141.1 |
| 2009/0047216 A1* | 2/2009 | Coukos | C12Q 1/6886 424/9.1 |

FOREIGN PATENT DOCUMENTS

| | | |
|---|---|---|
| WO | 2008-101118 | 8/2008 |
| WO | 2009-057849 | 5/2009 |

OTHER PUBLICATIONS

Bai et al. (Cancer Res. 2016, 76(21): 6396-6409).*
Gura (Science, 1997, 278:1041-1042).*
Kaiser (Science, 2006, 313: 1370).*
Chames et al (British J. of Pharmacology, 2009, 157, 220-233).*
Boscolo and Bischoff, "Vasculogenesis in infantile hemangioma." Angiogenesis 12(2), 197-207 (2009).
Buchner et al., "Identification of a new EGF-repeat-containing gene from human Xp22: a candidate for developmental disorders." Genomics, 2000 65(1):16-23.
Buckanovich et al., "Tumor Vascular Proteins As Biomarkers in Ovarian Cancer" J. Clin. Oncol., 2007, 25(7):852-861.
Calabrese et al., "A perivascular niche for brain tumor stem cells." 2007 Cancer Cell 11(1):69-82.
Lugassy et al., "Pilot Study on "Pericytic Mimicry" and Potential Embryonic/Stem Cell Properties of Angiotropic Melanoma Cells Interacting with the Abluminal Vascular Surface." Cancer Microenviron. 2013, 6(1): 19-29.
Chim et al., "EGFL6 promotes endothelial cell migration and angiogenesis through the activation of ERK." 2011 J. Biol. Chem. 286(25):22035-22046.
Deng et al., "Distinct Expression Levels and Patterns of Stem Cell Marker, Aldehyde Dehydrogenase Isoform 1 (ALDH1), in Human Epithelial Cancers." PLoS ONE 5, e10277 (2010).
Fujiwara et al., "The basement membrane of hair follicle stem cells is a muscle cell niche." 2011 Cell 144(4):577-589.
Gilbertson et al., "Making a tumour's bed: glioblastoma stem cells and the vascular niche." 2007 Cancer 7(10):733-736.
Holmberg et al., "EphB receptors coordinate migration and proliferation in the intestinal stem cell niche." 2006 Cell 125(6):1151-1163.
Khan et al., "Endothelial progenitor cells from infantile hemangioma and umbilical cord blood display unique cellular responses to endostatin." Blood, 2006, 108, 915-921.

(Continued)

Primary Examiner — Peter J Reddig
(74) Attorney, Agent, or Firm — Casimir Jones, SC

(57) ABSTRACT

The present invention determined that EGFL6 functions as a tumor vascular regulator of ovarian cancer stem cells (CSC). In addition, the present invention determined that a novel EGFL6 blocking antibody was able to restrict cancer cell growth and delay disease recurrence. As such, the present invention provides compositions and methods for inhibiting cancer cell growth, proliferation and/or metastasis. In particular, the present invention provides methods for inhibiting cancer cell growth, proliferation and/or metastasis through administration of a composition comprising an agent capable of inhibiting the function of EGFL6 (e.g., thereby inhibiting related cancer cell growth). In some embodiments, the agent capable of inhibiting the function of EGFL6 is an EGFL6 blocking antibody. The agents and related compositions additionally find use in diagnostic and research settings.

14 Claims, 8 Drawing Sheets

(56) References Cited

OTHER PUBLICATIONS

Khan et al., "Multipotential stem cells recapitulate human infantile hemangioma in immunodeficient mice." J Clin Invest, 2008, 118(7), 2592-2599.
Kryczek et al., "Expression of ALDH and CD133 defines ovarian cancer stem cells." Int J Cancer 130, 29-39 (2012).
Landen et al., "Targeting aldehyde dehydrogenase cancer stem cells in ovarian cancer." Mol Cancer Ther 9, 3186-3199 (2010).
Lu et al., "Gene Alterations Identified by Expression Profiling in Tumor-Associated Endothelial Cells from Invasive Ovarian Carcinoma." 2007 Cancer Research 67(4):1757-1768.
Oberauer et al. "EGFL6 is increasingly expressed in human obesity and promotes proliferation of adipose tissue-derived stromal vascular cells" 2010 Mol. Cell Biochem. 343(1-2):257-269.
Osada et al. "Expression of MAEG, a novel basement membrane protein, in mouse hair follicle morphogenesis." 2005 Exp Cell Res 303(1):148-159.
Scheres B., "Stem-cell niches: nursery rhymes across kingdoms." 2007 Nature Reviews Molecular Cell Biology 8(5):345-354.
Schmidt et al. "Epidermal growth factor-like domain 7 (EGFL7) modulates Notch signalling and affects neural stem cell renewal." Nat Cell Biol 2009, 11(7):873-880.
Shen et al., "Endothelial cells stimulate self-renewal and expand neurogenesis of neural stem cells." 2004 Science 304(5675):1338-1340.
Silva et al. "Aldehyde dehydrogenase in combination with CD133 defines angiogenic ovarian cancer stem cells that portend poor patient survival." Cancer Res (2011), 71(11):3991-4001.
Steg et al., "Stem Cell Pathways Contribute to Clinical Chemoresistance in Ovarian Cancer." Clin Cancer Res 18, 869-881 (2012).
Wang et al. "Analysis of Gene Expression Profiling in Meningioma: Deregulated Signaling Pathways Associated with Meningioma and EGFL6 Overexpression in Benign Meningioma Tissue and Serum." PLoS One, 2012, 7(12):e52707.
Wu et al. "Novel role for epidermal growth factor-like domain 7 in metastasis of human hepatocellular carcinoma." Hepatology 2009, 50(6):1839-1850.
Yeung et al., "Cloning of a novel epidermal growth factor repeat containing gene EGFL6: expressed in tumor and fetal tissues." 1999 Genomics 62(2):304-307.
International Search Report and Written Opinion, International Patent Application No. PCT/US2014/024070, dated Jun. 26, 2014.

* cited by examiner

US 9,850,300 B2

SEQUENCE LISTING

```
<160> NUMBER OF SEQ ID NOS: 7

<210> SEQ ID NO 1
<211> LENGTH: 10
<212> TYPE: PRT
<213> ORGANISM: Homo sapiens

<400> SEQUENCE: 1

Leu Arg Ala Pro Gly Thr Ile Lys Asp Arg
1               5                   10

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
cactcttcca gccttccttc c                                              21

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
ctcaggagga gcaatgatct tg                                             22

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cattgtccag cctaatgacg                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cagtcatcag ccccaaagag                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 6
gggagatgtg tgagaagtgc                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
ggtctggttg tcaggtttcc                                                   20
```

COMPOSITIONS AND METHODS RELATING TO INHIBITING CANCER CELL GROWTH AND/OR PROLIFERATION

CROSS-REFERENCE TO RELATED APPLICATIONS

The present application is a 371 U.S. National Phase Entry of pending International Application No. PCT/US2014/024070, filed Mar. 12, 2014, claims priority to U.S. Provisional Patent Application No. 61/790,138, filed Mar. 15, 2013, the contents of which are incorporated by reference in their entireties.

STATEMENT REGARDING FEDERALLY SPONSORED RESEARCH OR DEVELOPMENT

This invention was made with government support under OD004197 awarded by the National Institutes of Health. The Government has certain rights in the invention.

REFERENCE TO A SEQUENCE LISTING

Filed herewith and expressly incorporated herein by reference is a Sequence Listing submitted electronically as an ASCII text file via EFS-Web.

| File Name: | Size: | Created: |
|---|---|---|
| 33206-US-2-PCT_5T25.txt | 2,000 bytes | Sept. 9, 2015 |

FIELD OF THE INVENTION

The present invention determined that EGFL6 functions as a tumor vascular regulator of ovarian cancer stem cells (CSC). In addition, the present invention determined that a novel EGFL6 blocking antibody was able to restrict cancer cell growth and delay disease recurrence. As such, the present invention provides compositions and methods for inhibiting cancer cell growth, proliferation and/or metastasis. In particular, the present invention provides methods for inhibiting cancer cell growth, proliferation and/or metastasis through administration of a composition comprising an agent capable of inhibiting the function of EGFL6 (e.g., thereby inhibiting related cancer cell growth). In some embodiments, the agent capable of inhibiting the function of EGFL6 is an EGFL6 blocking antibody. The agents and related compositions additionally find use in diagnostic and research settings.

BACKGROUND OF THE INVENTION

Malignant lesions of the ovaries include primary lesions arising from normal structures within the ovary and secondary lesions from cancers arising elsewhere in the body. Primary lesions include epithelial ovarian carcinoma (70% of all ovarian malignancies), germ-cell tumors, sex-cord stromal tumors, and other more rare types. Metastases to the ovaries are relatively frequent, with the most common being from the endometrium, breast, colon, stomach, and cervix. Although many histologic types of ovarian tumors have been described, more than 90% of ovarian malignancies are epithelial tumors.

The precise cause of ovarian cancer is unknown, but several risk and contributing factors (including both reproductive and genetic factors) have been identified.

Ovarian cancer is the most common cause of cancer death from gynecologic tumors in the United States. Around the world, more than 200,000 women are estimated to develop ovarian cancer every year and about 100,000 die from the disease. The lifetime risk of a woman developing epithelial ovarian cancer is 1 in 70.

Early disease causes minimal, nonspecific, or no symptoms. Therefore, most cases are diagnosed in an advanced stage. The prognosis of ovarian cancer is closely related to the stage at diagnosis; thus, overall, prognosis for these patients remains poor.

Improved knowledge of ovarian cancer and methods for treating ovarian cancer are needed.

SUMMARY

Cancer stem cells (CSC) are closely associated with tumor vasculature in the CSC niche. Tumor vascular cells are known to provide critical growth, differentiation, and survival cues for CSC. Unfortunately little is known about the specific factors produced by vascular cells. EGFL6 is a factor specifically secreted by ovarian tumor vascular cells. EGFL6 is reported to regulate the differentiation of normal stem cells. In experiments conducted during the course of developing embodiments for the present invention, the impact of EGFL6 on ovarian cancer cell growth was examined. EGFL6 treatment was shown to increase phosphorylation of SRC kinase and SHP2 phosphatase, and significantly promote ovarian cancer cell growth. Single cell microfluidic culture demonstrated that EGFL6 promotes proliferation by stimulating ALDH+ CSC to undergo asymmetric division. Using a novel model of human tumor vasculature to express EGFL6 in the vascular niche, EGFL6 was shown to significantly promote ovarian tumor growth in vivo. Moreover, an EGFL6 blocking antibody was developed and it was found that anti-EGFL6 antibodies could restrict tumor growth and delay disease recurrences. Thus, EGFL6 is an import vascular regulator of ovarian CSC fate and EGFL6 blocking antibodies represent an important ovarian CSC targeting therapeutic.

Accordingly, the present invention determined that EGFL6 functions as a tumor vascular regulator of ovarian cancer stem cells (CSC). In addition, the present invention determined that a novel EGFL6 blocking antibody was able to restrict cancer cell growth and delay disease recurrence. As such, the present invention provides compositions and methods for inhibiting cancer cell growth, proliferation and/or metastasis. In particular, the present invention provides methods for inhibiting cancer cell growth, proliferation and/or metastasis through administration of a composition comprising an agent capable of inhibiting the function of EGFL6 (e.g., thereby inhibiting related cancer cell growth). In some embodiments, the agent capable of inhibiting the function of EGFL6 is an EGFL6 blocking antibody. The agents and related compositions additionally find use in diagnostic and research settings.

In certain embodiments, the present invention provides methods for inhibiting cancer cell proliferation, metastasis and/or growth comprising providing a sample comprising cancer cells expressing EGFL6 and exposing the sample to a composition comprising an agent capable of inhibiting EGFL6 function.

Such methods are not limited to a particular agent capable of inhibiting EGFL6 function. In some embodiments, the agent is an EGFL6 blocking antibody. In some embodiments, the EGFL6 blocking antibody is directed against an EGFL6 peptide. In some embodiments, the EGFL6 blocking antibody is directed against a peptide comprising the following amino acid sequence: LRAPGTIKDR (SEQ ID NO. 1).

Such methods are not limited to particular types of cancer cells. In some embodiments, the cancer cells are cancer stem cells. In some embodiments, the cancer cells are ovarian cancer cells. In some embodiments, the cancer cells are ovarian cancer stem cells. In some embodiments, the cancer cells are ALDH+ ovarian cancer stem cells.

Such methods are not limited to a particular type of sample. In some embodiments, the sample is an ex vivo sample, in vitro sample or an in vivo sample.

In some embodiments, the exposing of the sample to a composition comprising an agent capable of inhibiting EGFL6 function prevents phosphorylation of SRC kinase. In some embodiments, the exposing of the sample to a composition comprising an agent capable of inhibiting EGFL6 function prevents phosphorylation of SHP2 phosphatase. In some embodiments, the exposing of the sample to a composition comprising an agent capable of inhibiting EGFL6 function results in inhibition of proliferation, metastasis and/or growth of the cancer cells.

In certain embodiments, the present invention provides compositions comprising an antibody directed against an EGFL6 peptide. In some embodiments, the antibody is directed against the following amino acid sequence: LRAPGTIKDR (SEQ ID NO. 1).

In certain embodiments, the present invention provides methods for treating a subject suffering from a disorder affected by EGFL6 activity, comprising administering to the subject a composition comprising an agent capable of inhibiting EGFL6 function.

Such methods are not limited to a particular type of cancer. In some embodiments, the disorder is any type of cancer affected by EGFL6 activity. In some embodiments, the cancer is ovarian cancer. In some embodiments, the ovarian cancer comprises ovarian cancer stem cells. In some embodiments, the ovarian cancer stem cells comprise ALDH+ ovarian cancer stem cells.

In some embodiments, the agent is an EGFL6 blocking antibody capable of inhibiting EGFL6 function. In some embodiments, the EGFL6 blocking antibody is directed against an EGFL6 peptide. In some embodiments, the EGFL6 blocking antibody is directed against a peptide comprising the following amino acid sequence: LRAPGTIKDR (SEQ ID NO. 1).

In some embodiments, administration to the subject to the subject a composition comprising an agent capable of inhibiting EGFL6 function prevents phosphorylation of SRC kinase. In some embodiments, administration to the subject to the subject a composition comprising an agent capable of inhibiting EGFL6 function prevents phosphorylation of SHP2 phosphatase. In some embodiments, administration to the subject to the subject a composition comprising an agent capable of inhibiting EGFL6 function results in inhibition of proliferation, metastasis and/or growth of the cancer cells.

In some embodiments, the subject is a mammal (e.g., a human).

In some embodiments, one or more anti-cancer therapeutic agents are co-administered with the composition comprising an agent capable of inhibiting EGFL6 function.

Additional embodiments will be apparent to persons skilled in the relevant art based on the teachings contained herein.

Figure 5:
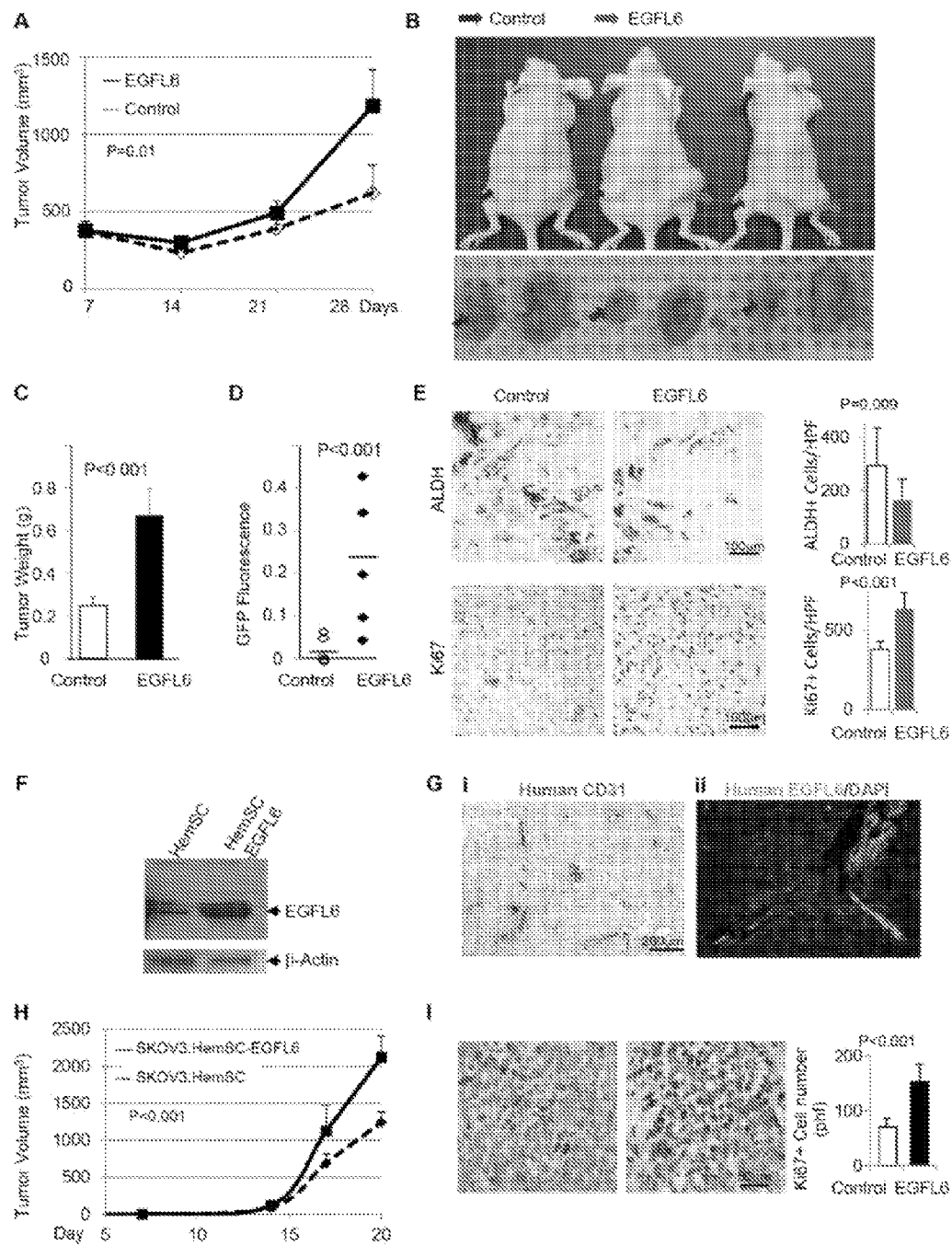

FIG. 5: EGFL6 expression promotes ovarian tumor growth in vivo. A-C, Increased Tumor growth in EGFL6-transfected ovarian cancer cells. A. Tumor volume. B. Tumor images. C. Tumor weight. D. GFP intensity plot of ovarian cancer cells transduced with EGFL6-GFP (EGFL6) or GFP alone (control). E. IHC analysis of quantification of ALDH and Ki67 expression in EGFL6 vs. control tumors. F. Western blot confirms EGFL6 expression in EGFL6-lentivirally transduced HemSCs. G (i) IHC shows human CD31+ vessels and (ii) IF shows EGFL6 expression in tumor vessels in SKOV3 ovarian tumor xenografts grown with infantile hemangioma stem cells (Hem-SC) expressing EGFL6. H. Tumor growth curves of SKOV3-HemSC-EGFL6 tumors vs. controls SKOV3-HemSC controls. I. IHC analysis of Ki67 expression in EGFL6-expressing vs. control tumors.

Figure 6:
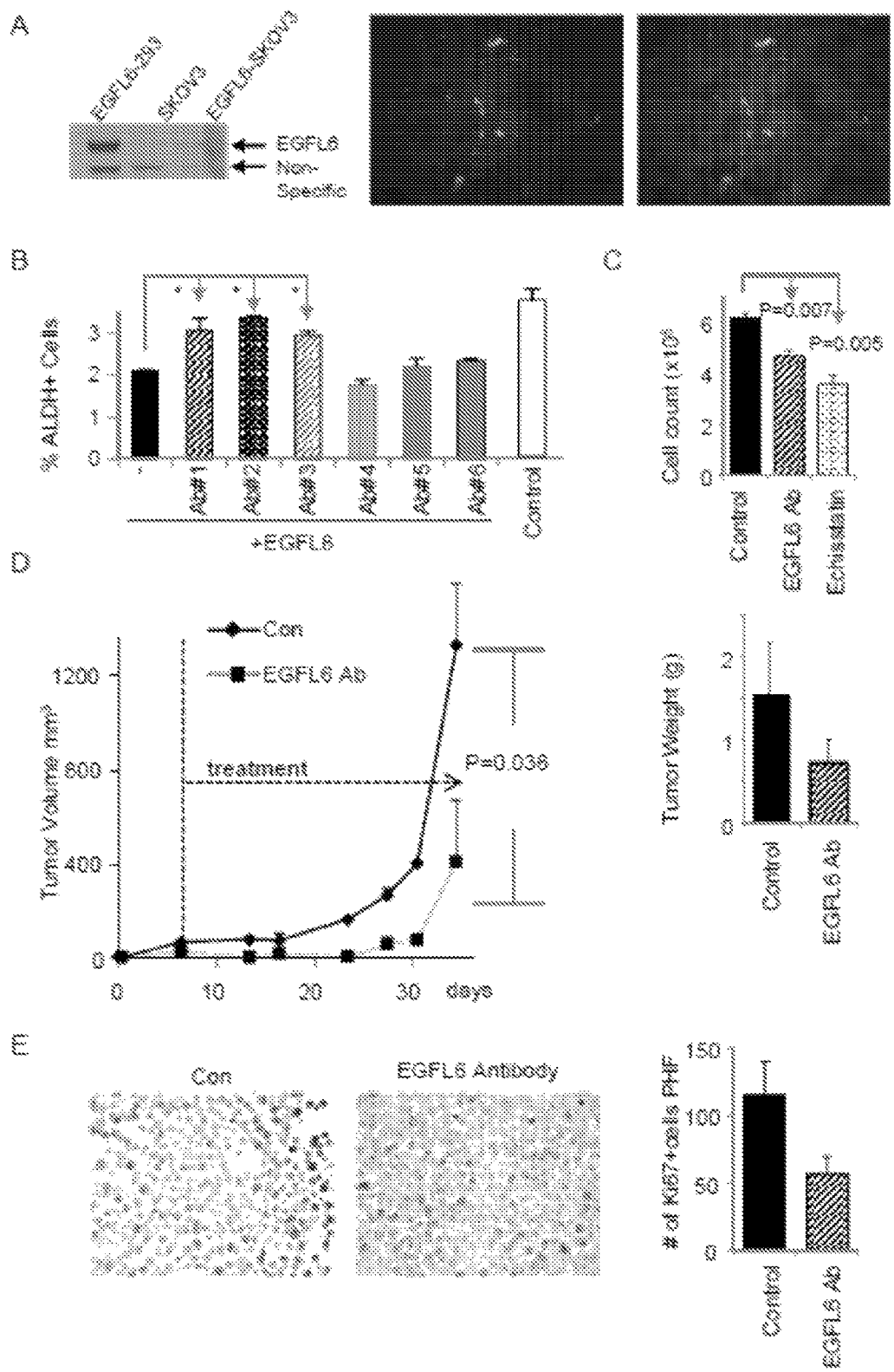

FIG. 6: EGFL6-blocking antibodies restrict tumor growth and delay tumor recurrence. A. Western blot and IF analysis with monoclonal anti-EGFL6 antibody demonstrating reactivity to stably transfected HEK293 and SKOV3 cells (EGFL6-293 and EGFL6-SKOV3 respectively). B. ALDH+ cell percentages when EGFL6 treatment is combined with 6 different anti-EGFL6 antibodies. C. Total cell numbers of A2008 control cells (endogenously express EGFL6) after 3 days of growth in the presence of Echistatin or EGFL6-blocking antibody. D. Tumor growth curves for SKOV3-HemSC-EGFL6 tumors in the presence/absence of EGFL6 blocking antibody. E. IHC analysis of Ki67 expression with EGFL6-blocking antibody treatment vs. control tumors.

Figure 7:
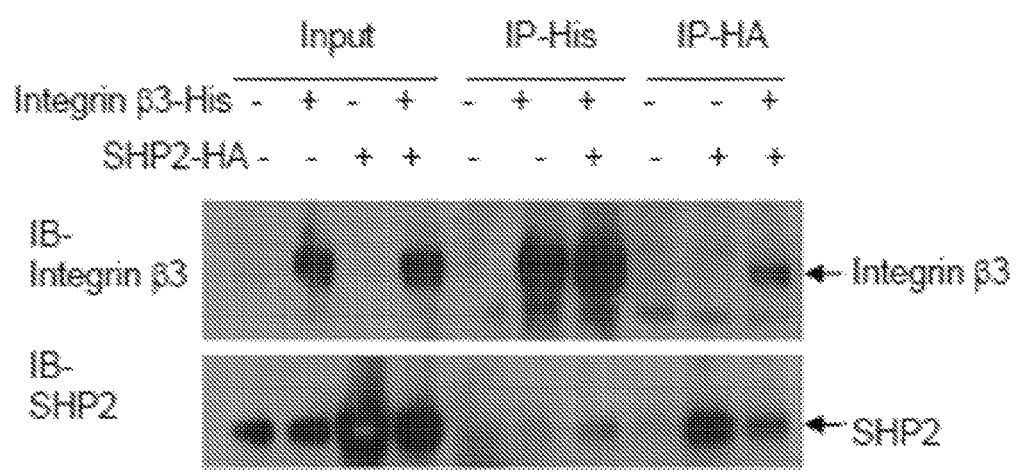

FIG. 7: Integrin β3 and SHP2 form immunocomplexes that can be pulled-down using antibodies recognizing either integrin β3 or SHP2.

Figure 8:
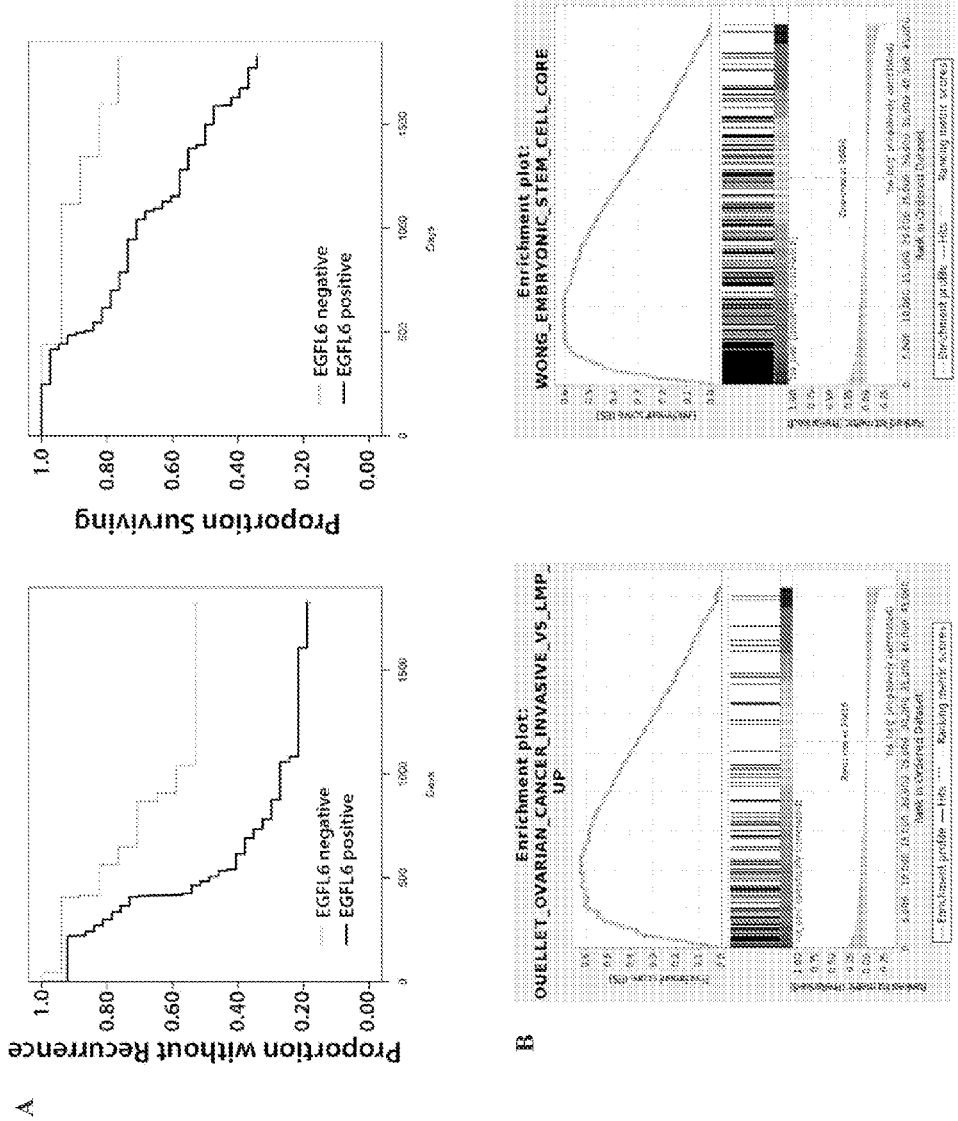

FIG. 8: EGFL6 expression portends a poor prognosis and correlates with ESC core gene expression. A. Kaplan Meier curves for recurrence free and overall survival for ovarian cancer patients with or without vascular EGFL6 expression in primary debulking specimens. B. Gene set enrichment analysis demonstrating EGFL6 correlated genes are associated with invasive ovarian cancer phenotype and an Embryonic Stem Cell core signature.

DEFINITIONS

To facilitate an understanding of the present invention, a number of terms and phrases are defined below.

As used herein, the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

The term "derivative" of a small molecule, as used herein, refers to a chemically modified small molecule wherein the chemical modification takes place either at a functional group of the small molecule (e.g., compound) or on the aromatic ring.

As used herein, the term "subject" refers to organisms to be treated by the methods and agents of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of an agent capable of inhibiting EGFL6 function) for purposes of inhibiting cancer cell growth and/or proliferation.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

In some embodiments, the "target cells" of the compositions and methods of the present invention include, refer to, but are not limited to cancer cells expressing cancer stem cells (e.g., ovarian cancer stem cells) (e.g., ALDH+ ovarian cancer stem cells).

As used herein, the term "co-administration" refers to the administration of at least two agent(s) (e.g., an agent of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the terms "non-specific binding" and "background binding" when used in reference to the interaction of a molecule with a protein or enzyme refers to an interaction that is not dependent on the presence of a particular structure.

As used herein, the term "modulate" refers to the activity of an agent (e.g., a peptide or small molecule of the present invention) to affect (e.g., to promote or retard) an aspect of cellular function, including, but not limited to, enzymatic activity, maturation, cell growth, replication, proliferation, and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

The present invention determined that EGFL6 functions as a tumor vascular regulator of ovarian cancer stem cells (CSC). In addition, the present invention determined that a novel EGFL6 blocking antibody was able to restrict cancer cell growth and delay disease recurrence. As such, the present invention provides compositions and methods for inhibiting cancer cell growth, proliferation and/or metastases. In particular, the present invention provides methods for inhibiting cancer cell growth, proliferation and/or metastases through administration of a composition comprising an agent capable of inhibiting the function of EGFL6 (e.g., thereby inhibiting related cancer cell growth). In some embodiments, the agent capable of inhibiting the function of EGFL6 is an EGFL6 blocking antibody. The agents and related compositions additionally find use in diagnostic and research settings.

Exemplary compositions and methods of the present invention are described in more detail in the following sections: I. The Role of EGFL6 within Cancer Cell Growth; II. Exemplary Agents; III. Therapeutic Applications; IV. Pharmaceutical Compositions, Formulations, and Exemplary Administration Routes and Dosing Considerations; and V. Drug Screens.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. The Role of EGFL6 within Cancer Cell Growth

Stem cells, in development and in the adult, appear to be closely associated with vascular cells in a 'stem cell niche' (see, e.g., Shen, et al., 2004 Science 304(5675):1338-1340; Holmberg, et al., 2006 Cell 125(6):1151-1163). Capillary endothelial cells secrete factors regulating stem cell self-renewal and fate (see, e.g., Shen, et al., 2004 Science 304(5675):1338-1340). Stem cells in turn secrete factors to maintain the endothelial cell survival and growth (see, e.g., Scheres 2007 Nature Reviews Molecular Cell Biology 8(5): 345-354). Like normal stem cells, cancer stem cells (CSC) also appear to have an important relationship with the vasculature (see, e.g., Calabrese, et al., 2007 Cancer Cell 11(1):69-82). CSC reside in a perivascular location tightly associated with tumor endothelial cells (see, e.g., Gilbertson, et al., 2007 Cancer 7(10):733-736). In fact CSC are highly angiogenic, secreting survival and proliferation signals to the tumor endothelial cells. Tumor vessels, which are known to be morphologically, functionally, and molecularly different from normal vessels, then provide an abnormal vascular niche; secreting factors which promote aberrant stem cell proliferation and further contribute to tumorigenesis. The tight co-association of tumor stem cells and vascular cells has led to the proposal of the vascular/stem cell niche as a therapeutic target (see, e.g., Gilbertson, et al., 2007 Cancer 7(10):733-736).

Unfortunately, little is known about the tumor vascular specific factors which regulate cancer stem cell fate. It was previously reported the expression profile of ovarian tumor vascular cells (see, e.g., Buckanovich, et al., 2007 J. Clin. Oncol. 25(7):852-861; Lu, et al., 2007 Cancer Research 67(4):1757-1768). These studies identified EGFL6 mRNA as upregulated in tumor vascular cells of epithelial ovarian cancer. Increased EGFL6 mRNA expression level was correlated with decreased disease-free survival of ovarian cancer patients (see, e.g., Buckanovich, et al., 2007 J. Clin. Oncol. 25(7):852-861).

EGFL6 is an extracellular protein harboring five signature EGF-repeats and an RGD domain (see, e.g., Yeung, et al., 1999 Genomics 62(2):304-307). It is mapped to human Xp22, a critical region for multiple developmental disorders (see, e.g., Buchner, et al., 2000 65(1):16-23). EGFL6 is primarily expressed in development with little or no reported expression in normal adult tissues (see, e.g., Buckanovich, et al., 2007 J. Clin. Oncol. 25(7):852-861; Yeung, et al., 1999 Genomics 62(2):304-307). Indeed, several studies indicate that EGFL6 plays a critical role in cellular proliferation and differentiation in different biologic systems; EGFL6 expression is involved in during osteoblast differentiation was found to to induce endothelial cell proliferation in an p-ERK dependent manner (see, e.g., Chim, et al., 2011 J. Biol. Chem. 286(25):22035-22046). Analogously, EGFL6 was reported to be induced during the differentiation of adipose tissue, and EGFL6 expression by adipose was found to promote the adhesion and proliferation of stromal vascular cells within the adipose tissue (see, e.g., Oberauer, et al., 2010 Mol. Cell Biochem. 343(1-2):257-269). Finally, EGLF6 is also expressed in the 'bulge' of the hair follicle, a site of stem cell differentiation, and is important in hair follicle morphogenesis (see, e.g., Osada, et al., 2005 Exp Cell Res 303(1):148-159; Fujiwara, et al., 2011 Cell 144(4): 577-589).

Experiments conducted during the course of developing embodiments for the present invention evaluated the role of EGFL6 in ovarian cancer. It was confirmed that EGFL6 is expressed in tumor endothelial cells. It was demonstrated that EGFL6 acts specifically on ALDH+ ovarian cancer stem cells (CSC) to promote cancer cell proliferation. Indeed, proliferation was shown to be increased due to 2-fold increase in ALDH+ cell asymmetric division, associated with an increase in total cell number, decreased percentage of ALDH+ cells, but an unchanged absolute number of CSC. Using a new model of human tumor vasculature it was demonstrated that vascular expression of EGFL6 promotes tumor growth in vivo. It was additionally shown that the increase in growth can be blocked by an EGFL6 blocking antibody. It was additionally shown that EGFL6 signaling is mediated in part via integrin mediated activation of the phosphatase SHP2.

Accordingly, in certain embodiments, the present invention provides compositions and methods for inhibiting cancer cell proliferation, metastases and/or growth through administration of a composition comprising an agent capable of inhibiting the function of EGFL6 (e.g., thereby inhibiting related cancer cell proliferation, metastases and/or growth).

The present invention is not limited to a particular manner of inhibiting the function of EGFL6 (e.g., thereby inhibiting related cancer cell proliferation and/or growth). In some embodiments, inhibiting the function of EGFL6 (e.g., thereby inhibiting related cancer cell proliferation and/or growth) is accomplished through inhibiting the function of EGFL6. In some embodiments, inhibiting the function of EGFL6 is accomplished through blocking/binding EGFL6 (e.g., with an EGFL6 blocking antibody). In some embodiments, inhibiting the function of EGFL6 is accomplished through blocking/hindering the target of EGFL6. In some embodiments, inhibiting the function of EGFL6 is accomplished through blocking/hindering an EGFL6 pathway related target including but not limited to activation of the phosphatase SHP2.

The present invention is not limited to inhibiting the proliferation and/or growth of a particular type of cancer cell through inhibiting of the function of EGFL6. In some embodiments, the cancer cells include cancer stem cells. In some embodiments, the cancer stems cells are ovarian cancer stem cells. In some embodiments, cancer stem cells are ALDH+ ovarian cancer stem cells. In some embodiments, the cancer cells are breast cancer cells. In some embodiments, the cancer cells are any type of cancer cell affected by EGFL6 activity.

II. Exemplary Agents Capable of Inhibiting EGFL6 Function

The present invention is not limited to a particular type of agent capable of inhibiting EGFL6 function.

In certain embodiments, the present invention provides an EGFL6 blocking antibody capable of binding with endogenous EGFL6 and thereby inhibiting its function. Indeed, experiments conducted during the course of developing embodiments for the present invention generated a EGFL6 blocking antibody and demonstrated that use of such EGFL6 blocking antibodies restricted tumor growth and delayed disease recurrence. The present invention is not limited to a particular type of EGFL6 blocking antibody. In some embodiments, the EGFL6 blocking antibody is a murine monoclonal antibody against EGFL6. In some embodiments, the EGFL6 blocking antibody is a murine monoclonal antibody against a peptide comprising the following amino acid sequence: LRAPGTIKDR (SEQ ID NO. 1). In some embodiments, the EGFL6 blocking antibody is a murine monoclonal antibody against a peptide comprising the at least a portion (e.g., 5%, 10%, 25%, 75%, 78%, 85%, 90%, 95%, 99.999%) of the following amino acid sequence: LRAPGTIKDR (SEQ ID NO. 1).

In some embodiments, the agent capable of inhibiting EGFL6 function is an EGFL6 specific siRNA. The present invention is not limited by the siRNA used. For example, in some embodiments, the present invention provides siRNAs of about 18-25 nucleotides long, 19-23 nucleotides long, or even more preferably 20-22 nucleotides long. The siRNAs may contain from about two to four unpaired nucleotides at the 3' end of each strand. In preferred embodiments, at least one strand of the duplex or double-stranded region of a siRNA is substantially homologous to or substantially complementary to a target RNA molecule (e.g., EGFL6). The present invention is not limited by the target RNA molecule/sequence. Indeed, a variety of target sequences are contemplated to be useful in the present invention including, but not limited to, 18-25 nucleotide stretches of the EGFL6 mRNA sequence (see, e.g., NCBI Accession No. NM_015507.3 and NCBI Accession No. NM_001167890.1).

III. Therapeutic Application

In certain embodiments, the present invention provides methods for treating a subject having suffering from a disorder affected by EGFL6 activity, comprising administering to the subject a composition comprising an agent capable of inhibiting EGFL6 function. In some embodiments, the disorder is any type of cancer affected by EGFL6 activity. In some embodiments, the cancer is ovarian cancer. In some embodiments, the cancer is breast cancer. In some embodiments, the disorder is any type of cancer. In some embodiments, the administration of the composition results in inhibited cancer cell growth and/or proliferation.

The methods are not limited to a particular type of agent capable of inhibiting EGFL6 function. In some embodiments, the agent is an EGLF6 blocking antibody. The present invention is not limited to a particular type of EGFL6 blocking antibody. In some embodiments, the EGFL6 blocking antibody is a murine monoclonal antibody against a peptide comprising the following amino acid sequence: LRAPGTIKDR (SEQ ID NO. 1). In some embodiments, the EGFL6 blocking antibody is a murine monoclonal antibody against a peptide comprising the at least a portion (e.g., 5%, 10%, 25%, 75%, 78%, 85%, 90%, 95%, 99.999%) of the following amino acid sequence: LRAPGTIKDR (SEQ ID NO. 1).

In some embodiments, the composition is co-administered with an additional therapeutic for treating cancer (e.g., a cancer therapeutic known for treating ovarian cancer). Indeed, it is a further aspect of this invention to provide methods for enhancing prior art therapies and/or pharmaceutical compositions by co-administering an agent capable of inhibiting EGFL6 function. In co-administration procedures, the agents may be administered concurrently or sequentially. In one embodiment, the agents described herein are administered prior to the other active agent(s). The pharmaceutical formulations and modes of administration may be any of those described below. In addition, the two or more co-administered chemical agents, biological agents or radiation may each be administered using different modes or different formulations.

A number of suitable therapeutic or anticancer agents are contemplated for use in the methods provided herein. Indeed, the methods provided herein can include but are not limited to, administration of numerous therapeutic agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of therapeutic agents such as chemotherapeutic compounds and anticancer therapies suitable for co-administration with the disclosed compounds are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods provided herein include one or more agents provided herein and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | |
|---|---|
| Aldesleukin (des-alanyl-1, serine-125 human interleukin-2) | Proleukin |
| Alemtuzumab (IgG1κ anti CD52 antibody) | Campath |
| Alitretinoin (9-cis-retinoic acid) | Panretin |
| Allopurinol (1,5-dihydro-4H-pyrazolo[3,4-d]pyrimidin-4-one monosodium salt) | Zyloprim |
| Altretamine (N,N,N',N',N'',N'',-hexamethyl-1,3,5-triazine-2,4,6-triamine) | Hexalen |
| Amifostine (ethanethiol, 2-[(3-aminopropyl)amino]-, dihydrogen phosphate (ester)) | Ethyol |
| Anastrozole (1,3-Benzenediacetonitrile, a,a,a',a'-tetramethyl-5-(1H-1,2,4-triazol-1-ylmethyl)) | Arimidex |
| Arsenic trioxide | Trisenox |
| Asparaginase (L-asparagine amidohydrolase, type EC-2) | Elspar |
| BCG Live (lyophilized preparation of an attenuated strain of *Mycobacterium bovis* (*Bacillus Calmette-Gukin* [BCG], substrain Montreal) | TICE BCG |
| bexarotene capsules (4-[1-(5,6,7,8-tetrahydro-3,5,5,8,8-pentamethyl-2-napthalenyl)ethenyl]benzoic acid) | Targretin |
| bexarotene gel | Targretin |
| Bleomycin (cytotoxic glycopeptide antibiotics produced by *Streptomyces verticillus*; bleomycin $A_2$ and bleomycin $B_2$) | Blenoxane |
| Capecitabine (5'-deoxy-5-fluoro-N-[(pentyloxy)carbonyl]-cytidine) | Xeloda |
| Carboplatin (platinum, diammine[1,1-cyclobutanedicarboxylato(2-)-0, 0']-,(SP-4-2)) | Paraplatin |
| Carmustine (1,3-bis(2-chloroethyl)-1-nitrosourea) | BCNU, BiCNU |
| Carmustine with Polifeprosan 20 Implant | Gliadel Wafer |
| Celecoxib (as 4-[5-(4-methylphenyl)-3-(trifluoromethyl)-1H-pyrazol-1-yl] benzenesulfonamide) | Celebrex |
| Chlorambucil (4-[bis(2chlorethyl)amino]benzenebutanoic acid) | Leukeran |
| Cisplatin ($PtCl_2H_6N_2$) | Platinol |
| Cladribine (2-chloro-2'-deoxy-b-D-adenosine) | Leustatin, 2-CdA |
| Cyclophosphamide (2-[bis(2-chloroethyl)amino]tetrahydro-2H-13,2-oxazaphosphorine 2-oxide monohydrate) | Cytoxan, Neosar |
| Cytarabine (1-b-D-Arabinofuranosylcytosine, $C_9H_{13}N_3O_5$) | Cytosar-U |
| cytarabine liposomal | DepoCyt |
| Dacarbazine (5-(3,3-dimethyl-1-triazeno)-imidazole-4-carboxamide (DTIC)) | DTIC-Dome |
| Dactinomycin, actinomycin D (actinomycin produced by *Streptomyces parvullus*, $C_{62}H_{86}N_{12}O_{16}$) | Cosmegen |
| Darbepoetin alfa (recombinant peptide) | Aranesp |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine |
| Denileukin diftitox (recombinant peptide) | Ontak |
| Dexrazoxane ((S)-4,4'-(1-methyl-1,2-ethanediyl)bis-2,6-piperazinedione) | Zinecard |

TABLE 1-continued

| | |
|---|---|
| Docetaxel<br>((2R,3S)-N-carboxy-3-phenylisoserine, N-tert-butyl ester,<br>13-ester with 5b-20-epoxy-12a,4,7b,10b,13a-<br>hexahydroxytax-11-en-9-one 4-acetate 2-benzoate,<br>trihydrate) | Taxotere |
| Doxorubicin HCl<br>(8S,10S)-10-[(3-amino-2,3,6-trideoxy-a-L-lyxo-<br>hexopyranosyl)oxy]-8-glycolyl-7,8,9,10-tetrahydro-6,8,11-<br>trihydroxy-1-methoxy-5,12-naphthacenedione<br>hydrochloride) | Adriamycin, Rubex |
| doxorubicin | Adriamycin PFS<br>Intravenous injection |
| doxorubicin liposomal | Doxil |
| dromostanolone propionate<br>(17b-Hydroxy-2a-methyl-5a-androstan-3-one propionate) | Dromostanolone |
| dromostanolone propionate | Masterone injection |
| Elliott's B Solution | Elliott's B Solution |
| Epirubicin<br>((8S-cis)-10-[(3-amino-2,3,6-trideoxy-a-L-arabino-<br>hexopyranosyl)oxy]-7,8,9,10-tetrahydro-6,8,11-trihydroxy-<br>8-(hydroxyacetyl)-1-methoxy-5,12-naphthacenedione<br>hydrochloride) | Ellence |
| Epoetin alfa<br>(recombinant peptide) | Epogen |
| Estramustine<br>(estra-1,3,5(10)-triene-3,17-diol(17(beta))-, 3-[bis(2-<br>chloroethyl)carbamate] 17-(dihydrogen phosphate),<br>disodium salt, monohydrate, or estradiol 3-[bis(2-<br>chloroethyl)carbamate] 17-(dihydrogen phosphate),<br>disodium salt, monohydrate) | Emcyt |
| Etoposide phosphate<br>(4'-Demethylepipodophyllotoxin 9-[4,6-O-(R)-ethylidene-<br>(beta)-D-glucopyranoside], 4'-(dihydrogen phosphate)) | Etopophos |
| etoposide, VP-16<br>(4'-demethylepipodophyllotoxin 9-[4,6-0-(R)-ethylidene-<br>(beta)-D-glucopyranoside]) | Vepesid |
| Exemestane<br>(6-methylenandrosta-1,4-diene-3,17-dione) | Aromasin |
| Filgrastim<br>(r-metHuG-CSF) | Neupogen |
| floxuridine (intraarterial)<br>(2'-deoxy-5-fluorouridine) | FUDR |
| Fludarabine<br>(fluorinated nucleotide analog of the antiviral agent<br>vidarabine, 9-b-D-arabinofuranosyladenine (ara-A)) | Fludara |
| Fluorouracil, 5-FU<br>(5-fluoro-2,4(1H,3H)-pyrimidinedione) | Adrucil |
| Fulvestrant<br>(7-alpha-[9-(4,4,5,5,5-penta fluoropentylsulphinyl)<br>nonyl]estra-1,3,5-(10)-triene-3,17-beta-diol) | Faslodex |
| Gemcitabine<br>(2'-deoxy-2',2'-difluorocytidine monohydrochloride (b-<br>isomer)) | Gemzar |
| Gemtuzumab Ozogamicin<br>(anti-CD33 hP67.6) | Mylotarg |
| Goserelin acetate | Zoladex Implant |
| Hydroxyurea | Hydrea |
| Ibritumomab Tiuxetan<br>(immunoconjugate resulting from a thiourea covalent bond<br>between the monoclonal antibody Ibritumomab and the<br>linker-chelator tiuxetan [N-[2-bis(carboxymethyl)amino]-3-<br>(p-isothiocyanatophenyl)-propyl]-[N-[2-<br>bis(carboxymethyl)amino]-2-(methyl)-ethyl]glycine) | Zevalin |
| Idarubicin<br>(5,12-Naphthacenedione, 9-acetyl-7-[(3-amino-2,3,6-<br>trideoxy-(alpha)-L-lyxo-hexopyranosyl)oxy]-7,8,9,10-<br>tetrahydro-6,9,11-trihydroxyhydrochloride, (7S-cis)) | Idamycin |
| Ifosfamide<br>(3-(2-chloroethyl)-2-[(2-chloroethyl)amino]tetrahydro-2H-<br>1,3,2-oxazaphosphorine 2-oxide) | IFEX |
| Imatinib Mesilate<br>(4-[(4-Methyl-1-piperazinyl)methyl]-N-[4-methyl-3-[[4-(3-<br>pyridinyl)-2-pyrimidinyl]amino]-phenyl]benzamide<br>methanesulfonate) | Gleevec |
| Interferon alfa-2a<br>(recombinant peptide) | Roferon-A |

TABLE 1-continued

| | |
|---|---|
| Interferon alfa-2b (recombinant peptide) | Intron A (Lyophilized Betaseron) |
| Irinotecan HCl ((4S)-4,11-diethyl-4-hydroxy-9-[(4-piperi-dinopiperidino)carbonyloxy]-1H-pyrano[3',4':6,7] indolizino[1,2-b]quinoline-3,14(4H,12H)dione hydrochloride trihydrate) | Camptosar |
| Letrozole (4,4'-(1H-1,2,4-Triazol-1-ylmethylene)dibenzonitrile) | Femara |
| Leucovorin (L-Glutamic acid, N[4[[(2amino-5-formyl1,4,5,6,7,8-hexahydro4oxo6-pteridinyl)methyl]amino]benzoyl], calcium salt (1:1)) | Wellcovorin, Leucovorin |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol |
| Lomustine (1-(2-chloro-ethyl)-3-cyclohexyl-1-nitrosourea) | CeeNU |
| Mechlorethamine, nitrogen mustard (2-chloro-N-(2-chloroethyl)-N-methylethanamine hydrochloride) | Mustargen |
| Megestrol acetate 17α(acetyloxy)-6-methylpregna-4,6-diene-3,20-dione | Megace |
| Melphalan, L-PAM (4-[bis(2-chloroethyl)amino]-L-phenylalanine) | Alkeran |
| Mercaptopurine, 6-MP (1,7-dihydro-6H-purine-6-thione monohydrate) | Purinethol |
| Mesna (sodium 2-mercaptoethane sulfonate) | Mesnex |
| Methotrexate (N-[4-[[(2,4-diamino-6-pteridinyl)methyl]methylamino]benzoyl]-L-glutamic acid) | Methotrexate |
| Methoxsalen (9-methoxy-7H-furo[3,2-g][1]-benzopyran-7-one) | Uvadex |
| Mitomycin C | Mutamycin |
| mitomycin C | Mitozytrex |
| Mitotane (1,1-dichloro-2-(o-chlorophenyl)-2-(p-chlorophenyl) ethane) | Lysodren |
| Mitoxantrone (1,4-dihydroxy-5,8-bis[[2-[(2-hydroxyethyl)amino]ethyl]amino]-9,10-anthracenedione dihydrochloride) | Novantrone |
| Nandrolone phenpropionate | Durabolin-50 |
| Nofetumomab | Verluma |
| Oprelvekin (IL-11) | Neumega |
| Oxaliplatin (cis-[(1R,2R)-1,2-cyclohexanediamine-N,N'][oxalato(2-)-O,O']platinum) | Eloxatin |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL |
| Pamidronate (phosphonic acid (3-amino-1-hydroxypropylidene) bis-, disodium salt, pentahydrate, (APD)) | Aredia |
| Pegademase ((monomethoxypolyethylene glycol succinimidyl) 11-17-adenosine deaminase) | Adagen (Pegademase Bovine) |
| Pegaspargase (monomethoxypolyethylene glycol succinimidyl L-asparaginase) | Oncaspar |
| Pegfilgrastim (covalent conjugate of recombinant methionyl human G-CSF (Filgrastim) and monomethoxypolyethylene glycol) | Neulasta |
| Pentostatin | Nipent |
| Pipobroman | Vercyte |
| Plicamycin, Mithramycin (antibiotic produced by *Streptomyces plicatus*) | Mithracin |
| Porfimer sodium | Photofrin |
| Procarbazine (N-isopropyl-μ-(2-methylhydrazino)-p-toluamide monohydrochloride) | Matulane |
| Quinacrine (6-chloro-9-(1-methyl-4-diethyl-amine)butylamino-2-methoxyacridine) | Atabrine |
| Rasburicase (recombinant peptide) | Elitek |

TABLE 1-continued

| | |
|---|---|
| Rituximab (recombinant anti-CD20 antibody) | Rituxan |
| Sargramostim (recombinant peptide) | Prokine |
| Streptozocin (streptozocin 2-deoxy-2-[[(methylnitrosoamino)carbonyl]amino]-a(and b)-D-glucopyranose and 220 mg citric acid anhydrous) | Zanosar |
| Talc ($Mg_3Si_4O_{10}$ $(OH)_2$) | Sclerosol |
| Tamoxifen ((Z)2-[4-(1,2-diphenyl-1-butenyl)phenoxy]-N,N-dimethylethanamine 2-hydroxy-1,2,3-propanetricarboxylate (1:1)) | Nolvadex |
| Temozolomide (3,4-dihydro-3-methyl-4-oxoimidazo[5,1-d]-as-tetrazine-8-carboxamide) | Temodar |
| teniposide, VM-26 (4'-demethylepipodophyllotoxin 9-[4,6-0-(R)-2-thenylidene-(beta)-D-glucopyranoside]) | Vumon |
| Testolactone (13-hydroxy-3-oxo-13,17-secoandrosta-1,4-dien-17-oic acid[dgr]-lactone) | Teslac |
| Thioguanine, 6-TG (2-amino-1,7-dihydro-6H-purine-6-thione) | Thioguanine |
| Thiotepa (Aziridine, 1,1',1''-phosphinothioylidynetris-, or Tris(1-aziridinyl)phosphine sulfide) | Thioplex |
| Topotecan HCl ((S)-10-[(dimethylamino)methyl]-4-ethyl-4,9-dihydroxy-1H-pyrano[3',4':6,7]indolizino[1,2-b]quinoline-3,14-(4H,12H)-dione monohydrochloride) | Hycamtin |
| Toremifene (2-(p-[(Z)-4-chloro-1,2-diphenyl-1-butenyl]-phenoxy)-N,N-dimethylethylamine citrate (1:1)) | Fareston |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar |
| Trastuzumab (recombinant monoclonal $IgG_1$ kappa anti-HER2 antibody) | Herceptin |
| Tretinoin, ATRA (all-trans retinoic acid) | Vesanoid |
| Uracil Mustard | Uracil Mustard Capsules |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar |
| Vinblastine, Leurocristine ($C_{46}H_{56}N_4O_{10} \cdot H_2SO_4$) | Velban |
| Vincristine ($C_{46}H_{56}N_4O_{10} \cdot H_2SO_4$) | Oncovin |
| Vinorelbine (3',4'-didehydro-4'-deoxy-C'-norvincaleukoblastine[R-(R*,R*)-2,3-dihydroxybutanedioate (1:2)(salt)]) | Navelbine |
| Zoledronate, Zoledronic acid ((1-Hydroxy-2-imidazol-1-yl-phosphonoethyl)phosphonic acid monohydrate) | Zometa |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In some embodiments, methods provided herein comprise administering one or more agents provided herein (an agent capable of inhibiting EGFL6 function) with radiation therapy. The methods provided herein are not limited by the types, amounts, or delivery and administration systems used to deliver therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in therapeutic period. In one embodiment, radiation is initiated in week 1 or week 2, and is administered for the remaining duration of therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

In some embodiments of the methods provided herein, one or more agents provided herein and one or more therapeutic agents or anticancer agents are administered to a subject (e.g., animal) under one or more of the following conditions: at different periodicities, at different durations, at different concentrations, by different administration routes, etc. In some embodiments, the agent capable of inhibiting EGFL6 function is administered prior to therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of therapeutic or anticancer agent. In some embodiments, the agent capable of inhibiting EGFL6 function is administered after therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the agent capable of inhibiting EGFL6 function and therapeutic or anticancer agent are administered concurrently but on different schedules, e.g., the agent is administered daily while therapeutic or anticancer agent is administered once a week, once every two weeks, once every three weeks, or once every four weeks. In other embodiments, the agent capable of inhibiting EGFL6 function is administered once a week while therapeutic or anticancer agent is administered daily, once a week, once every two weeks, once every three weeks, or once every four weeks.

IV. Pharmaceutical Compositions, Formulations, and Exemplary Administration Routes and Dosing Considerations Exemplary embodiments of various contemplated medicaments and pharmaceutical compositions are provided below.

A. Preparing Medicaments

It is contemplated that the agents of the present invention (e.g., agents capable of inhibiting EGFL6 activity) (e.g., EGFL6 blocking antibodies) are useful in the preparation of medicaments to treat a variety of conditions associated with EGFL6 activity.

In addition, it is contemplated that the agents are also useful for preparing medicaments for treating other disorders wherein the effectiveness of the agents are known or predicted. The methods and techniques for preparing medicaments of an agent of the present invention (e.g., agents capable of inhibiting EGFL6 activity) (e.g., EGFL6 blocking antibodies) are well-known in the art. Exemplary pharmaceutical formulations and routes of delivery are described below.

One of skill in the art will appreciate that any one or more of the agents described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions (e.g., comprising agents capable of inhibiting EGFL6 activity (e.g., EGFL6 blocking antibodies)) are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In some embodiments, the agents of the present invention are provided in unsolvated form or are in non-aqueous solutions (e.g., ethanol). The agents may be generated to allow such formulations through the production of specific crystalline polymorphs compatible with the formulations.

In certain embodiments, the present invention provides instructions for administering an agent to a subject. In certain embodiments, the present invention provides instructions for using the compositions contained in a kit for the treatment of conditions characterized by the dysregulation of apoptotic processes in a cell or tissue (e.g., providing dosing, route of administration, decision trees for treating physicians for correlating patient-specific characteristics with therapeutic courses of action). In certain embodiments, the present invention provides instructions for using the compositions contained in the kit to treat a variety of disorders associated with EGFL6 function.

C. Exemplary Administration Routes and Dosing Considerations

Various delivery systems are known and can be used to administer therapeutic agents (e.g., exemplary agents as described in Section II above) of the present invention (e.g., agents capable of inhibiting EGFL6 activity) (e.g., EGFL6 blocking antibodies), e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the agents identified can be administered to subjects or individuals susceptible to or at risk of developing a variety of conditions associated with EGFL6 activity (e.g., ovarian cancer). When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent, the effective amount may be more or less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-administration Routes and Dosing Considerations

The present invention also includes methods involving co-administration of the agents described herein (e.g., agents capable of inhibiting EGFL6 activity) (e.g., EGFL6 blocking antibodies) with one or more additional active agents (e.g., anti-cancer agents described in Section III). Indeed, it is a further aspect of this invention to provide methods for enhancing prior art therapies and/or pharmaceutical compositions by co-administering the agents of this invention. In co-administration procedures, the agents may be administered concurrently or sequentially. In one embodiment, the agents described herein are administered prior to the other active agent(s). The pharmaceutical formulations and modes of administration may be any of those described above. In addition, the two or more co-administered chemical agents, biological agents or radiation may each be administered using different modes or different formulations.

V. Drug Screens

In some embodiments of the present invention, potential agents (e.g., peptides, small molecules, peptidomimetics, and/or cyclic peptides) are screened for their binding affinity to EGFL6. In some embodiments, binding affinity screens are conducted in in vitro systems. In other embodiments, these screens are conducted in in vivo or ex vivo systems. In some embodiments, structure-based virtual screening methodologies are contemplated for predicting the binding affinity of potential agents (e.g., peptides, small molecules, peptidomimetics, and/or cyclic peptides) with EGFL6. In some embodiments, small molecule structures are predicted from a molecular modeling software (e.g., MacroModel, MOE, Glide, Gold, Autodock, DOCK, Unity, Cerius2, Daylight, PipelinePilot, ChemAxon, Sprout, Hook, MCSS, AMBER, BOSS).

EXPERIMENTAL

The following example is provided in order to demonstrate and further illustrate certain preferred embodiments and aspects of the present invention and is not to be construed as limiting the scope thereof.

Example 1

This example describes expression of EGFL6 in normal human and ovarian tumor vessels. Two tumor vascular profiling studies reported EGFL6 mRNA is significantly upregulated in the vasculature of ovarian tumors. The expression of EGFL6 mRNA in tumor endothelial cells versus tumor associated myeloid cells and cancer cells from 3 primary ovarian cancers was first confirmed. RT-PCR confirmed EGFL6 expression in tumor endothelial cells. Similarly RT-PCR of ovarian tumor cell lines demonstrated no expression in SKOV3, A2780, HEY1, OVCAR3, and OVCAR8 cells lines, however some expression was detectable in the A2008 cell line. IHC confirmed expression of EGFL6 in CD31 expressing ovarian tumor vascular cells. IHC screening in a panel of normal tissues demonstrated EGFL6 expression was also significantly expressed in vessels within the colonic vessels and normal ovaries. Weak expression was noted within the kidney. No expression was observed in heart, muscle, liver, lung, or spleen.

Example 2

Figure 1:
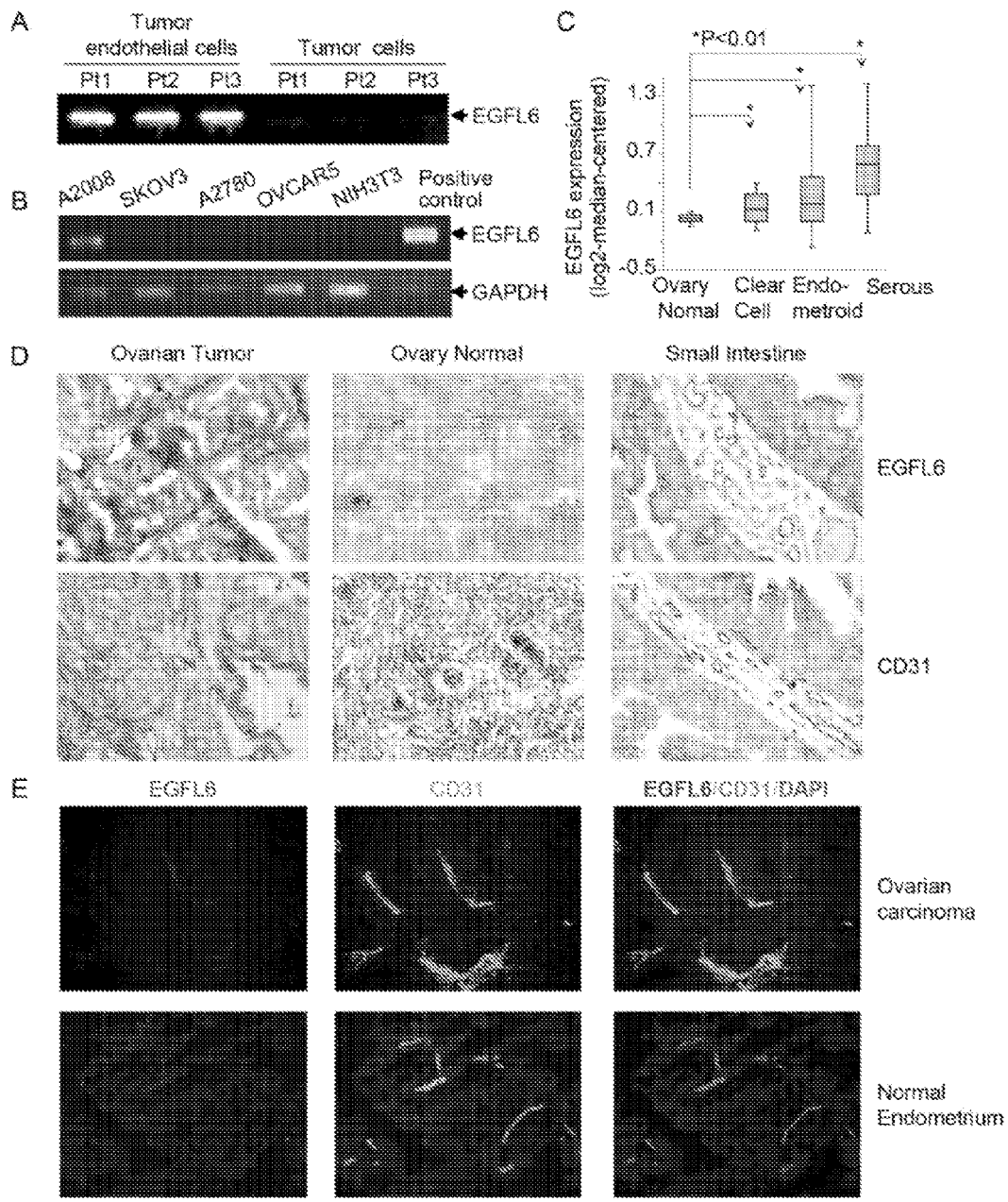
FIG. 1: Expression of EGFL6 in ovarian tumors and normal tissue. A and B. RT-PCR showing EGFL6 is expressed in tumor endothelial cells, and not expressed in primary tumor cells. EGFL6 is expressed in A2008, but not other ovarian cancer cell lines. C. Expression of EGFL6 in sub-types of ovarian cancers demonstrating significant up-regulation in serous ovarian adenocarcinoma (GSE6008, ONCOMINE). D. IHC shows EGFL6 expression patterns in human ovarian tumor vessels, normal ovaries, and small intestine. E. Immunofluorescence (IF) shows EGFL6 expression in tumor endothelium, also identified by CD31 staining, and absent from the normal endometrium (DAPI staining of nucleus).

This example demonstrates that EGFL6 protein is expressed in ovarian tumor vascular cells and portends a poor prognosis. The expression of EGFL6 mRNA in tumor endothelial cells versus ovarian cancer cells was first confirmed. RT-PCR demonstrated EGFL6 expression in 3/3 primary tumor endothelial cell specimens (FIG. 1A). SKOV3, A2780, HEY1, OVCAR3, and OVCAR8 ovarian cancer cells lines demonstrated no EGFL6 expression; expression was detectable in the A2008 cell line (FIG. 1B). Immunohistochemical analysis of EGFL6 in ovarian tumors confirmed primarily vascular expression. However, EGFL6 was detected in rare cancer cells, in tumor associated adipose, and in rare isolated stromal cells (FIG. 1C). Co-immunofluorescence of EGFL6 and CD31 confirmed that EGFL6 expression was primarily in tumor vascular cells (FIG. 1E).

EGFL6 mRNA expression in the ONCOMINE cancer database was also analyzed (see, e.g., Rhodes, D. R., et al. Neoplasia 9, 166-180 (2007)). EGFL6 mRNA levels are significantly elevated in all ovarian tumor histologies, but are greatest in serous tumors (FIG. 1C).

A TMA of 54 ovarian tumors with two different anti-EGFL6 antibodies was next stained. Vascular EGFL6 expression was scored as present or absent in each tumor and then performed multivariate analysis to determine if EGFL6 vascular EGFL6 protein expression was a prognostic factor for ovarian cancer. An aggregated variable for EGFL-6 overexpression in either primary or metastatic tissue was used (When available). Suggesting a potential important biological role for EGFL6, univariate proportional hazards regression showed EGFL-6 expression was related both to death (hazard ratio=3.91, p=0.01) and recurrence (hazard ratio=2.67, p=0.01) (FIG. 8A). Multiple proportional hazards regression was next used to determine if EGFL-6 expression was significant while controlling fix age, stage, tumor grade, and optimal debulking No dependence between tumor stage and EGFL-6 level (p=0.70) or tumor grade and EGFL-6 level (p=0.50) was found. It was found that the presence of EGFL6 in primary debulking specimens was an independent biomarker of significantly shorter progression free survival and overall survival, suggesting a potentially important biologic role for EGFL6.

In order to explore the potential function of EGFL6 RNAseq data from 261 TCGA serous ovarian carcinomas were screened and investigated the correlation of expression of EGFL6 to all other genes in the genome. Spearman correlation was performed comparing expression of EGFL6 to the expression of all other genes in the Ensmbl genome database (55,840 genes). A p-value cutoff of 1e-8 was applied to generate a list of the 538 most correlated genes. Numerous tumor vascular specific markers (including MXRA, TDO2, TNFAIP6, SEMA3D, and Col11A1) and EGF like genes (including EGFLAM and MEGF10) were also highly correlated with EGFL6 expression. Gene set enrichment analysis demonstrated the EGFL6 correlated genes were strongly correlated with invasive ovarian cancer and embryonic stem cell core genes (FIG. 8B).

Example 3

Figure 2:
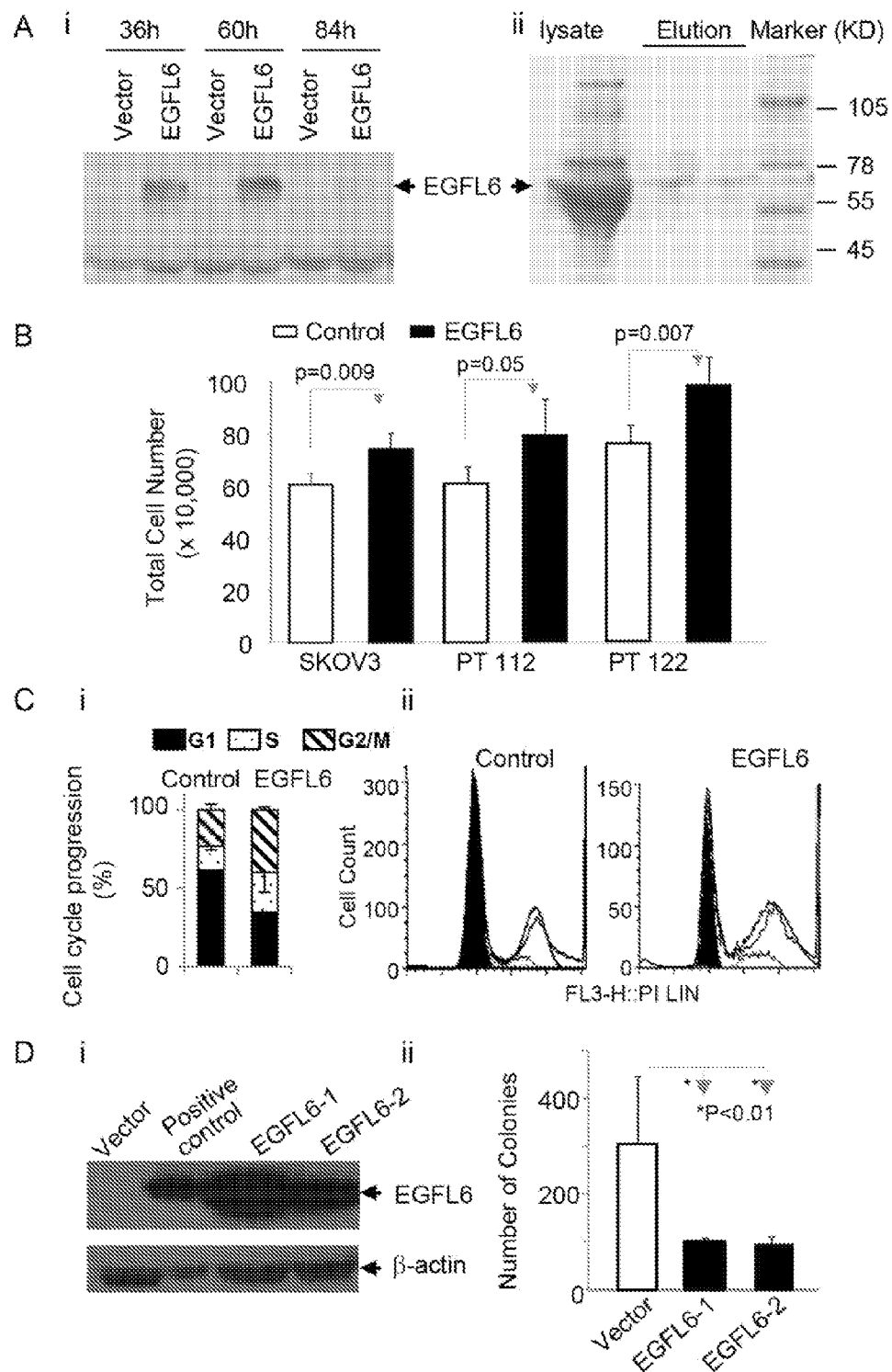
FIG. 2: Effect of EGFL6 on ovarian cancer cell proliferation. Ai. Western blot of EGFL6 in supernatant from control and EGFL6 transfected HEK293 cells at the indicated time points posttransfection. ii. Coomassie stain of the steps of EGFL6 purification. B. Total cell number, EGFL6-treated vs. control, in SKOV3 cell line and primary tumor cells (PT112 and PT122). C. Cell cycle analysis of EGFL6-treated SKOV3 cells; i. Summary of 3 independent analyses and ii. Representative cell cycle profile. D. Effect of EGFL6 on colony formation in soft agar assay. i. Western blot shows expression of EGFL6 (Flag-tagged) in two stably transfected SKOV3 clones. ii. Number of colonies formed in EGFL6-SKOV3 clones vs. vector control-transfected SKOV3 cells using soft agar assays.

This example demonstrates that EGFL6 induces ovarian cancer cell proliferation. EGFL6 was next expressed in HEK293 cells, NIH3T3 cells, and SKOV3 ovarian cancer cells. Western blot analysis confirmed secretion of EGLF6 in both transient and stable transfectants (FIG. 2Ai, 2D) from all three cell lines. EGFL6 protein was purified to >95% purity (FIG. 2Aii) and treated ovarian cancer cells with either purified EGFL6, supernatant from EGFL6-expressing HEK293 cells, or supernatant from control transfected HEK293 cells. Purified fusion protein and supernatant from EGFL6 transfected cells had similar effects. EGFL6 treatment of SKOV3, OVCAR3, OVCAR8, and primary ovarian tumor cells was associated with a 30-40% increase in total cell number (FIG. 2B). Cell cycle analysis demonstrated that EGFL6 treatment was associated with a ~20% decrease in the number of cells in G1 phase, and a concomitant increase in the number of cells in S and G2/M phases (FIG. 2C).

Given the ability of ELGF6 to promote cell growth, the oncogenic potential of EGFL6 using soft agar assays was assessed. It was observed that EGFL6 expression had no impact on the growth of NIH3T3 cells. Surprisingly, in three different stably transfected EGFL6 expressing SKOV3 clones tested, a reduction in the number and size of colonies formed was observed.

Example 4

Figure 3:
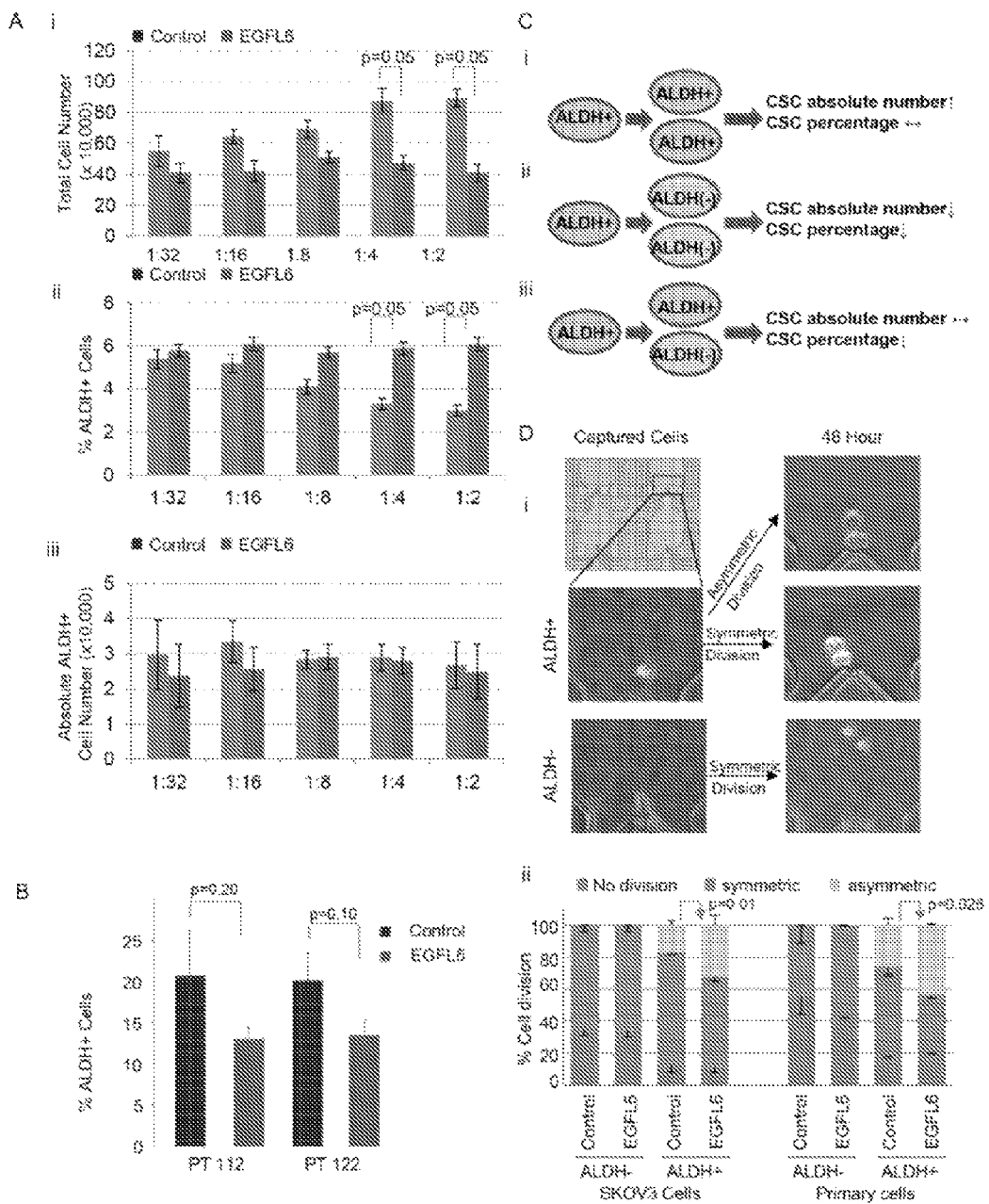
FIG. 3: EGFL6 promotes ALDH+ cell asymmetric division. A. Summary of replicate experiments demonstrating EGFL6 treatment is associated with (i) increasing total cell numbers, (ii) decreasing percentages of ALDH+ cells, but (iii) no change in absolute ALDH+ cell number. B. EGFL6-treated vs. control—percentages of ALDH+ cells from cultured primary ovarian cancer. C. Cartoon illustrating changes in CSC number and percentage as a result of symmetric vs. asymmetric cell division (↑: increase. ↓: decrease. ↔: no change). D. Microfluidic culture traces CSC cell division. i. Top left demonstrates low power microscopic image of isolated cells in microfluidic culture. Bottom left shows ALDEFLUOR stain in situ confirms the identity of ALDH+ vs. ALDH(−) cells. Right panels indicate representative images of the observed types of division. ii. Cell division outcomes for ALDH(−) vs. ALDH+ cells under EGFL6-treated vs. control conditions, in SKOV3 and primary cells.

This example demonstrates that EGFL6 promotes asymmetric division of ALDH$^+$ ovarian CSCs. Given GSEA analysis demonstrates a strong correlation of EGFL6 with core stem cell factors, the impact of EGFL6 on ovarian CSCs was next assessed. It has been shown that aldehyde dehydrogenase enzymatic activity (ALDH) is an excellent marker of ovarian CSCs in SKOV3 cells and primary patient samples (see, e.g., Silva, I. A., et al. Cancer Res (2011); Landen, C. N., Jr., et al. Mol Cancer Ther 9, 3186-3199 (2010); Steg, A. D., et al. Clin Cancer Res 18, 869-881 (2012); Kryczek, I., et al. Int J Cancer 130, 29-39 (2012); Deng, S., et al. PLoS ONE 5, e10277 (2010)). The impact of EGFL6 treatment on the percentage of ALDH$^+$ CSCs in vitro was next assessed. Treatment of ovarian cancer cells with increasing concentrations of EGFL6 was associated with increasing total cell numbers, but decreasing percentages of ALDH$^+$ CSCs (FIG. 3Ai-ii). However, given the increase in total cell numbers, the absolute ALDH$^+$ CSC number remained unchanged (FIG. 3Aiii). Similarly, stably transfected SKOV3 cells, which constitutively express EGFL6, were found to have increased growth rates, but reduced percentages of ALDH$^+$ cells. Human ovarian cancer ascites cells were also treated with EGFL6 in a tumor sphere assay. Once again, treatment with EGLF6 was associated with a reduction in ALDH$^+$ cell percentages in tumor spheres (FIG. 3B).

A dividing ALDH$^+$ CSC can theoretically undergo at least three distinct types of cell division: (i) symmetric division yielding 2 ALDH$^+$ cells, (ii) differentiation yielding 2 ALDH$^{(-)}$ cells, or (iii) asymmetric division yielding an ALDH$^+$ cell (self-maintenance) and an ALDH$^{(-)}$ cell (FIG. 3C). The finding that EGFL6 increases total cancer cell number and decreases the percentage of ALDH$^+$ cells while not impacting the absolute number of ALDH$^+$ cells suggests would be consistent with EGFL6 stimulation of ALDH$^+$ CSC asymmetric division. Alternatively, EGFL6 could preferentially promote proliferation of ALDH− cells.

To determine if EGFL6 is promoting asymmetric division, a novel microfluidic culture device was used which allows the isolation, confirmation, and culture of individual cells. ALDH$^+$ and ALDH$^{(-)}$ SKOV3 cells were FACS-sorted into separate microfluidic devices (see, e.g., Chung, J., Kim, Y. J. & Yoon, E. Appl Phys Lett 98, 123701 (2011)), and confirmed ALDH expression with fluorescent microscopy (FIG. 3Di). Cells were then mock-treated or treated with EGFL6. After 48 hours, live cells were stained using ALDE-FLUOR and re-imaged using fluorescent microscopy (FIG. 3Dii, right panels). Cell divisions, type of daughter cell (ALDH$^{(-)}$ or ALDH$^+$), and total cell number were assessed. Approximately 35% of untreated ALDH$^{(-)}$ SKOV3 cells demonstrated no cell division (FIG. 3Dii) while 65% underwent symmetric division to produce two ALDH$^{(-)}$ cells. Production of ALDH$^+$ daughter cells from ALDH$^{(-)}$ cells was not observed. EGFL6 treatment of ALDH$^{(-)}$ SKOV3 cells had no significant impact on the number or type of cell divisions. Only 10% of untreated ALDH$^+$ SKOV3 cells did not divide. Unlike ALDH$^{(-)}$ cells, ALDH$^+$ cells demonstrated the ability to undergo both symmetric division, yielding two ALDH$^+$ cells, and asymmetric division, yielding one ALDH$^+$ cell and one ALDH$^{(-)}$ cell. EGFL6 treatment of ALDH$^+$ SKOV3 cells resulted in a 2-fold increase in the percentage of ALDH$^+$ cells undergoing asymmetric division (FIG. 3D). This was associated with a statistically significant increase in total cell numbers; 6.5 versus 3.7 average cells/well and total 325 vs. 185 total cells/50 captured cells in EGFL6 treated and control ALDH$^{(+)}$ cells respectively.

These results were next confirmed with two separate primary cell samples. For primary cells, it was observed that over 50% of untreated ALDH$^{(-)}$ cells underwent no division over 5 days, while remaining cells underwent symmetric division. EGFL6 treatment of ALDH$^{(-)}$ cells was associated with a non-statistically significant increase in symmetric divisions. 20% of ALDH$^+$ cells underwent no division. EGFL6 treatment of primary ALDH$^+$ cells was associated with a 1.9-fold increase in the number of ALDH⁺ cells undergoing asymmetric division (FIG. 3Dii). EGFL6 treatment was associated with an increase in total cell numbers (90 EGFL6 treated cells yielded 585 total cells while 82 mock-treated cells yielded 451 cells).

Example 5

This example demonstrates that EGFL6 co-localizes with integrins and its function is blocked by the Integrin inhibitor Echistatin. EGFL family members have been reported signal via integrins (REF). EGFL6 contains a putative integrin binding RGD motif. To determine if EGFL6 may signal on ALDH+ CSC via integrin binding, qRT-PCR analysis of integrin family mNRA expression in ALDH+ and ALDH− ovarian cancer cells was performed. It was found that Integrin $\beta 3$ (ITGB3), but not other integrins, was specifically enriched in ALDH+ SKOV3 and A2008 cells. In line with the enrichment of Integrin $\beta 3$ in CSCs, a significant down-regulation of Integrin $\beta 3$ in EGFL6-expressing SKOV3 cells was observed where CSCs population were reduced. To confirm the importance of these results in human tumors, co-immunofluorescence with EGFL6 and Integrin $\beta 3$ was next performed. Both EGFL6 and Integrin $\beta 3$ co-localized human in ovarian tumor vasculature and in rare tumor cells.

To explore whether EGFL6 could be signaling via binding with integrins, the impact of the integrin inhibitor Echistatin on EGFL6 mediated reductions in the percentage of ALDH+ CSC was assessed. While treatment with EGFL6 reduced ALDH+ populations as observed earlier pretreatment of the cells with Echistatin inhibited the effect of EGFL6. Once again similar results were obtained with the A2780 cell line.

Lastly, EGFL6 mediated signal activation was evaluated. Integrin signaling has been reported to induce the thoughts correlation of FAK, SRC and SHP2 among others. Western blot analysis of EGFL6 treated ALDH+ and ALDH− SKOV3 cells demonstrated increased levels of p-SHP2 in ALDH+ cells. Treatment with EGFL6 associated with a further increase in p-SHP2 levels. A modest increase in p-FAK and p-SRC levels was observed. Phosphorylation of all of these proteins could be blocked with Echistatin.

Example 6

Figure 4:
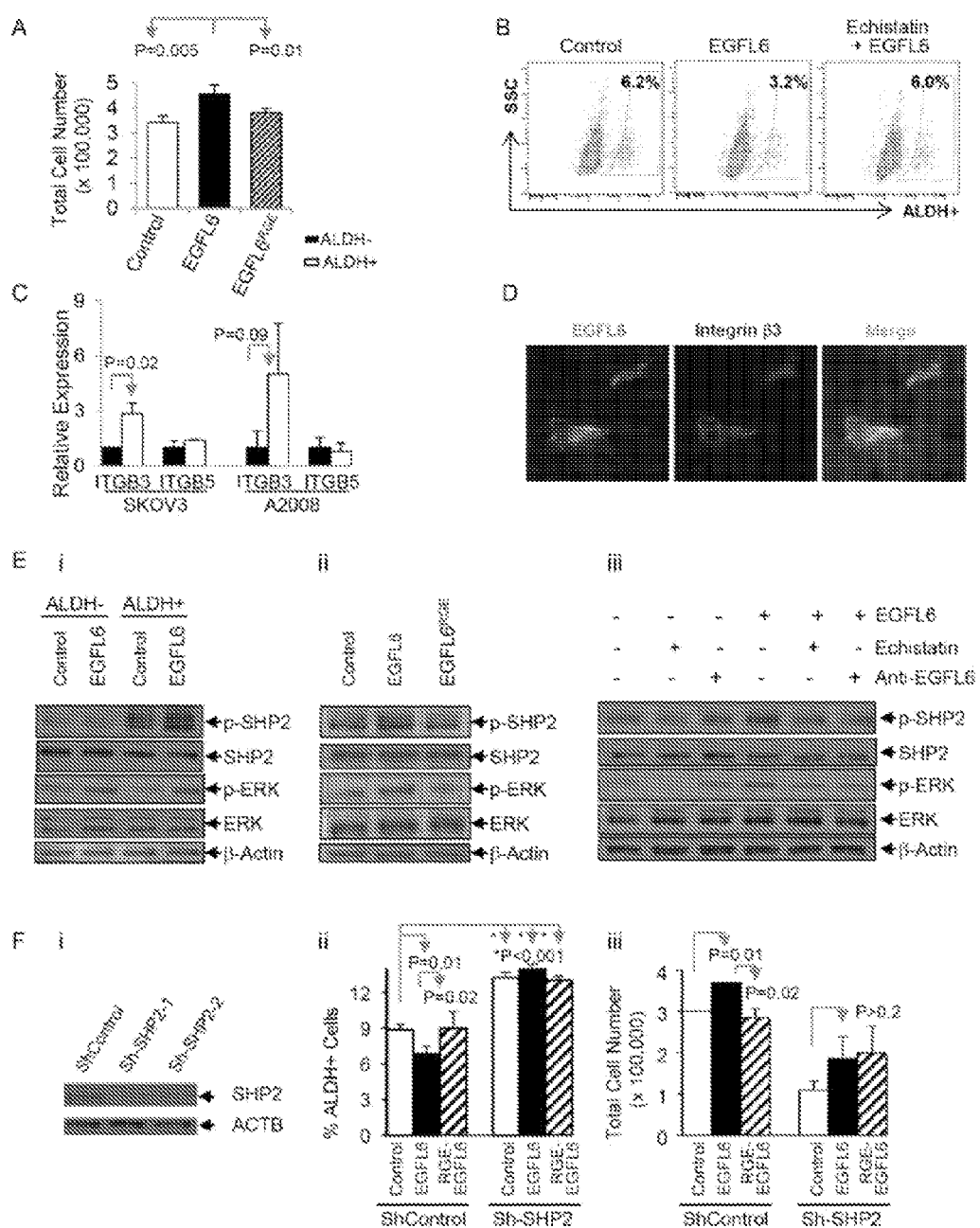
FIG. 4: EGFL6 signals through Integrins and SHP2. A. Mutation of EGFL6-RGD motif to RGE suppressed EGFL6-mediated cell proliferation in SKOV3 cells. B. Integrin blockade with the competitive inhibitor Echistatin inhibits EGFL6-mediated reduction in ALDH+ cell percentages. C. Integrin β3 (ITGB3) and β5 (ITGB5) mRNA levels in ALDH(−) vs. ALDH+ ovarian cancer cells. D. IF co-localization of EGFL6 and Integrin β3 in ovarian tumors. E. EGFL6 treatment is associated with phosphorylation of SHP2 and ERK. i. SHP2 is preferentially phosphorylated in ALDH+ cells and EGFL6 further increases SHP2 activation in ALDH+ cells. EGFL6 treatment is associated with increase p-ERK in both ALDH+ and ALDH(−) cells. ii. EGFL6-RGE mutant does not increase p-SHP2 or p-ERK. iii. EGFL6-mediated SHP2 and ERK phosphorylation is suppressed by Echistatin and anti-EGFL6 antibody treatment. F. SHP2 knockdown inhibits EGFL6-mediated reduction in ALDH+ cell percentages. i. Western Blot confirms SHP2 knockdown. ii. SHP2 knockdown eliminated EGFL6 effect on ALDH+ percentage. iii. SHP2 knockdown inhibited EGFL6-induced SKOV3 cell proliferation.

This example demonstrates that EGFL6 Signaling Requires RGD binding and SHP2 activation. EGFL6 activity has been reported to be dependent on an intact RGD domain (see, e.g., Chim, S. M., et al. J Biol Chem 286, 22035-22046 (2011)), suggesting signaling via Integrins. To determine if EGFL6 signaling on cancer cells is via integrin bind, an EGFL6 protein with an RDG-to-RGE mutation (EGFL6$^{RGE}$) was generated. Mutation of the RGD domain eliminated the proliferative effects of EGFL6 (FIG. 4A). Similarly, pretreatment of SKOV3 cells with the integrin $\beta 1/\beta 3$ inhibitor Echistatin blocked both EGFL6-mediated cancer cell proliferation and the decrease in ALDH⁺ percentage (FIG. 4B). Together these data suggest integrin binding is necessary for EGFL6 signaling.

To identify integrin family members potentially involved in EGFL6 signaling, qRT-PCR analysis of integrin family mRNA expression in ALDH⁺ and ALDH⁽⁻⁾ ovarian cancer cells was performed. It was found that Integrin $\beta_3$ (ITGB3), but not Integrin $\beta_5$, was specifically enriched in ALDH⁺ SKOV3 and A2008 cells (FIG. 4C). To confirm the importance of these results in human tumors, co-immunofluorescence with EGFL6 and Integrin $\beta_3$ was next performed. Both EGFL6 and Integrin $\beta_3$ co-localized in human ovarian tumor vasculature and in rare tumor cells (FIG. 4D).

Cellular signaling changes associated with EGFL6 was next examined. Western blot analysis of ALDH⁺ and ALDH⁽⁻⁾ SKOV3 cells demonstrated increased levels of p-SHP2 in ALDH⁺ cells vs. ALDH⁽⁻⁾ cells. EGFL6 treatment was associated with increased p-SHP2 levels specifically in ALDH⁺ cells (FIG. 4Ei). EGFL6$^{RGE}$ did not increase p-SHP2 levels (FIG. 4Eii). SHP2 phosphorylation could be blocked with Echistatin (FIG. 4Eiii) or an EGFL6-blocking antibody. SHP2 phosphorylation was associated with increased p-ERK levels (4Ei-iii).

Co-immunoprecipitation (Co-IP) studies were next performed to determine if SHP2 is directly interacting with Integrin b3. Co-IP with confirmed previous reports that integrin $\beta 3$ and SHP2 form immunocomplexes that can be pulled-down using antibodies recognize either integrin $\beta 3$ or SHP2 (FIG. 7). To confirm a critical role for SHP2 in EGFL6-signaling on ovarian CSCs, shRNA knockdown of SHP2 was next performed. Knockdown of SHP2 with two independent shRNA was associated with a significant decrease in total cell numbers (FIG. 4F). Interestingly, SHP2 knockdown was associated with an increase in ALDH⁺ cell percentages, suggesting a potential reduction in asymmetric divisions (FIG. 4F). SHP2 knockdown blocked EGFL6 induced cell proliferation (FIG. 4Fii-iii).

Example 7

This examples demonstrates that EGFL6 promotes tumor growth in vivo. In vivo tumor growth of two stably transfected EGFL6-expressing SKOV3 clones was next assessed. Both clones demonstrated increased growth rates relative to SKOV3 vector only controls (FIG. 5A-C). Similarly, SKOV3 cells transduced with lentivirus EGFL6-GFP, compared to GFP-only control, demonstrated increased tumor growth based on both tumor weight and GFP intensity (FIG. 5D). EGFL6-expressing tumors demonstrated a 2-fold increase in percentage of Ki67-expressing cells (FIG. 5E, bottom) and a slight reduction in the percentage of ALDH⁺ cells in EGFL6-expressing tumor (FIG. 5E, top).

While some EGFL6 expression was observed in tumor cells, EGFL6 is predominantly expressed in tumor vasculature. To determine the impact of vascular EGFL6 expression on tumor growth, a new tumor model with EGFL6 expressing human tumor vascular cells was created. EGFL6 was expressed in human infantile hemangioma stem cells (HemSC). HemSC proliferate and generate blood filled human vessels in vivo (see, e.g., Boscolo, E. & Bischoff, J. Angiogenesis 12, 197-207 (2009); Khan, Z. A., et al. J Clin Invest 118, 2592-2599 (2008); Khan, Z. A., et al. Blood 108, 915-921 (2006)). Western blot confirmed strong EGFL6 expression in EGFL6-lentivirally transduced HemSC (FIG. 5F). When SKOV3 and HemSC-EGFL6 cells were co-injected in vivo, robust human CD31⁺ tumor vessels which expressed EGFL6 was observed (FIG. 5G). SKOV3 cells grown with control HemSC-EGFL6 cells demonstrated increased growth compared to SKOV3 cells grown with HemSC controls (FIG. 5H). As observed with ectopic EGFL6 expression, expression of EGFL6 by HemSC cells was associated with increased numbers of Ki67⁺ cells (FIG. 5I).

To confirm our findings were not specific to cell lines, primary cells from three different patient samples were co-injected (n=2 each) with HemSC-EGFL6 cells or controls HemSC. It was observed tumor initiation from 4 of 6 HemSC-EGFL6 tumors compared to 1 of 6 control HemSC tumors. For the one patient for which a control HemSC tumor formed, HemSC-EGFL6 co-injected tumor cells grew larger and more rapidly.

Example 8

This example describes developing of an EGFL6-Blocking antibody. Data suggest that EGFL6 plays an important role in promoting ovarian cancer cell proliferation. As such, it may be a therapeutic target. Monoclonal antibodies targeting EGFL6 were developed. Antibodies were confirmed by both western blot and immunohistochemistry (FIG. 6A). Antibodies were then screened for the ability to inhibit EGFL6 activity. Three of six antibodies generated demonstrated (i) the ability to block EGFL6-mediated reductions in ALDH$^+$ cell percentages (FIG. 6B), (ii) a reduction in cellular proliferation rates in A2008 cells (which endogenously express EGFL6, FIG. 6C), and (iii) the ability to block the increased phosphorylation of SHP2 and p-ERK (FIG. 4Eiii).

Finally, the impact of anti-EGFL6 therapy in vivo was evaluated. SKOV3-HemSC-EGFL6 tumors were generated as above and then treated via intraperitoneal injection twice weekly with purified anti-EGFL6 or mIgG control. Anti-EGFL6 treatment was associated with a significant reduction in tumor growth (FIG. 6D). Anti-EGFL6 treatment was associated with statistically significant reduction in Ki67 staining (FIG. 6E).

Example 9

This example demonstrates that EGFL6 promotes cellular migration. EGF factors have been reported to enhance the migration and invasion of various cell populations. The impact of EGFL6 on cellular migration was therefore assessed. Using simple in vitro scratch test would healing assays it was observed that EGFL6 treated cells demonstrate a 40% increase in the rate of wound closure. In order to confirm this 'wound healing' was attributable to increased cellular migration and not secondary to increased cellular proliferation, traditional transwell migration assays with EGFL6 protein as a chemoattractant was used. Once again increased cellular migration in the presence of EGFL6 was observed. Finally, a novel microfluidics device was used to determine the impact of EGFL6 on the migration of individual cells. To more specifically assess the impact on ovarian CSC versus progenitors, ALDH+ and ALDH− cells were sorted and loaded into individual channels of a microfluidics device in which migration could be directly monitored. EGFL6 was added to a reservoir at one side of the device to create a gradient of expression. EGFL6 had no impact on the migration of ALDH(−) cells. However, ALDH+ cells demonstrated robust migration towards EGFL6. These results demonstrate that EGFL6 promotes the cellular migration of ALDH+ CSC.

Example 10

This example describes the materials and methods for Examples 1-9.
Cell Culture and Treatment SKOV3, A2008, and A2780 were maintained in RPMI-1640, supplemented with 10% FBS with 1% Penicillin/Streptomycin, and cultured in humidified atmosphere of 5% $CO_2$ at 37° C. For all in vitro cell culture experiments, isolated cells were allow to recover overnight following FACS, prior to treatment. Infantile Hemangioma Stem cells were maintained in EBM-2 medium with growth factor supplement cocktails in culture plates coated with fibronectin. For Echistatin and EGFL6 treatment, cells were pretreated with Echistatin (Sigma, 100 nM) for 24 hours prior to EGFL6 treatment. All transfections were performed using FuGene6 reagent (Promega) per company protocol.
TMA Staining The Applicants used a tissue microarray (TMA) of 56 ovarian cancer patient specimens from chemotherapy naïve patients' primary debulking surgeries. 7 (12.5%), 6 (10.7%), 37 (66.1%), and 6 (10.7%) patients had stage I-IV disease, respectively. Median age 58 years (minimum; 30; maximum, 84). TMA sections were processed as previously described (SILVA) with two different anti-EGL6 antibodies (Sigma 1:200 and a mouse anti-EGFL6 antibody we generated 1:400). Tumors were independently scored by tow reviewers. Any discordance was discusses and a single conclusion reached. Tumors were scored as EGFL6+ if vascular EGFL6 expression was detected in either primary tumor or omental tumor sites. The product limit method of Kaplan and Meier was used to estimate overall and recurrence-free survival. Follow-up time was calculated from the date of diagnosis/staging surgery until the date first documented relapse or death. Patients who did not reach either endpoint at 5 were censored on their last known follow-up date. Comparisons of EGFL6 expression groups (present or absent) with the estimated overall or recurrence-free survival by were conducted using the log-rank test statistic with a P value <5% as a significantly meaningful differences between groups.
Generating EGFL6-Expressing Cell Lines EGFL6 was cloned into two different vectors: p3×FLAG (for transfection) and pRSV-GFP (for lentiviral infection). To establish EGFL6-transfected clones, cells were transfected with EGFL6-p3×FLAG. EGFL6-expressing clones were selected by G418 treatment and confirmed by western blotting with Flag antibody. Transduced cell lines expressing EGFL6 or control were obtained by lentiviral infection followed by FACS sorting of GFP-positive cells.
EGFL6 Production and Treatment:

HEK293 cells were transiently transfected with EGFL6 plasmid using FuGENE 6 reagent per company protocol (Promega) in growth medium containing 5% FBS. Supernatant was collected at 36 hr and replaced with new medium; then collected at 72 hr. Peak EGFL6 secretion was confirmed at 72 hr by western blotting analysis. Supernatant from 72 hr collection was used for cell treatment with EGFL6. Control supernatant was collected at 72 hr from empty vector transfected cells.

To obtain purified EGFL6, recombinant EGFL6-flag protein was expressed by transient transfection of HEK293 cells and purified with Anti-FLAG M2 Affinity Gel (Sigma). Briefly, cell lysate was loaded onto the FLAG M2 Affinity Gel column under gravity flow on ice, and washed with 10-20 column volumes of TBS. The bound FLAG-EGFL6 fusion protein was eluted with 0.1 M glycine HCl, pH 3.5, into vials containing 20 µL 1 M Tris, pH 8.0 to neutralize pH. Eluted FLAG-EGFL6 fusion protein was used immediately or stored at −80° C.
Cell Cycle Analysis SKOV3 cells were seeded at $5 \times 10^5$ in 6 cm culture plates, synchronized by serum starvation for 24 hrs, then treated with EGFL6 or control for 24 hrs. Cells were fixed with ice-cold alcohol, washed with PBS, and stained with propidium iodine (10 mg/ml) and RNase A (100 ug/ml) in PBS for 1 hr at 30° C. Cell cycle profile was acquired by FACS analysis and data were analyzed by Flowjo.

Tumor Sphere Assays

Sphere culture was performed as previously described (see, e.g., Silva, I. A., et al. Cancer Res (2011)). Briefly, single cell suspensions were plated in triplicate in ultra-low attachment plates (Corning, Acton, Mass., USA) in serum-free MEBM-2 (Lonza). Cells were plated at the indicated density and from 1,000-10,000 cells/ml in subsequent passage. Sphere formation was assessed 2 weeks after seeding cells.

Soft Agar Colony Formation Assay

Base agar was prepared as 4 ml of 0.5% agarose (Noble agar, BD Biosciences) in complete cell culture medium containing 1 mg/ml G418 per 60 mm culture plate. After the base agar was set, equal volume of top agar were prepared with final concentration of 0.35% agar mixed with cells in same medium. $2 \times 10^4$ NIH3T3 or SKOV3 cells expressing EGFL6 or vector control were seeded per plate. Each sample was prepared in triplicate. The plates were incubated at 37oC for up to 2 weeks. Cell colonies were visualized by staining with 0.005% crystal violet and the number of colonies was counted under phase-contrast microscope.

Quantitative Real-Time PCR (qRT-PCR)

Total RNA was isolated from whole cells or FACS-isolated cells using RNeasy mini or Plus Micro (for cell number<$1 \times 10^5$) kits (Qiagen). cDNA was synthesized using Superscript III First-Strand Synthesis System (Invitrogen). qRT-PCR reactions were set up in replicate with the SYBR Green Master (AB Biosystems). Each sample was repeated 3 times and analyzed with β-actin as internal control. Primer sequences: ACTB (forward, 5'-CACTCTTCCAGCCTTC-CTTCC-3' (SEQ ID NO. 2); reverse, 5'-CTCAGGAGGAG-CAATGATCTTG-3') (SEQ ID NO. 3); ITGB3 (forward 5'-CATTGTCCAGCCTAATGACG-3' (SEQ ID NO. 4); reverse, 5'-CAGTCATCAGCCCCAAAGAG-3' (SEQ ID NO. 5)); ITGB5 (forward, 5'-GGGAGATGTGT-GAGAAGTGC-3' (SEQ ID NO. 6); reverse, 5'-GGTCTG-GTTGTCAGGTTTCC-3' (SEQ ID NO. 7)).

Flow Cytometry and Fluorescence Associated Cell Sorting (FACS)

FACS assay was performed as previously described (see, e.g., Silva, I. A., et al. Cancer Res (2011)). Briefly, SKOV3 cells or primary ovarian tumor/ascetics cells were stained for ALDH using ALDEFLUOR kit per company protocol (Stem Cell Technologies). DAPI staining was used to exclude non-viable cells. For FACS cell sorting, equal number of ALDH and ALDH$^{(-)}$ cells were collected for subsequent experiments.

Immunohistochemistry (IHC) and Immunofluorescence (IF)

Experiments performed as previously described (see, e.g., Silva, I. A., et al. Cancer Res (2011)). Primary antibodies—anti-EGFL6 (Sigma), anti-CD31 (Abcam), anti-ALDH (BD Pharmingen)—were used at 1:100 dilutions. Anti-ITGB3 (Millipore), Goat anti-rabbit IgG conjugated to AF488 (Molecular probes, Carlsbad, Calif., A21424, 1:200) and goat anti-mouse IgG conjugated to AF648 (Molecular probes, A21237) were used for fluorescent detection.

EGFL6 Antibody Purification and Treatment

EGFL6 monoclonal antibody producing hybridoma cells were maintained in RPMI medium supplemented with 10% FBS. For antibody purification, the cells were cultured in reduced FBS (5%). Culture supernatant was collected and cell debris was removed by centrifugation. EGFL6 antibody was pulled down using Protein G Agarose heeds, Fast Flow (Millipore), washed and eluded with 50 mM glycine PH.2.7. Antibody solution was immediately neutralized to PH 7.2-7.4 with Tris (Ph 9.0, final concentration 25 mM). NaCl was added to final concentration of 150 mM. EGFL6 antibody was applied at 5 μg/ml for in vitro cell treatment and 50 μg/mouse for in vivo treatment.

SHP2 shRNA Knockdown

ShP2 shRNA (Sigma) and control scrambled shRNA were transfected into SKOV3 per manufacturer's recommendation. Cell lysates were prepared after 48 hr for western blot to confirm SHP2 knockdown. For EGFL6 treatment, cells were treated with EGFL6 24 hr post-transfection for 36 hr before collected for analysis.

Murine Tumor Models with Ectopic EGFL6 Expression in Ovarian Cancer Cells

All animal experiments were conducted in accordance with institutional guidelines of the University of Michigan, and the studies were approved by the University Committee for Use and Care of Animals. For transfected EGFL6-SKOV3 tumor model, three G418-selected EGFL6-SKOV3 clones or three empty-vector clones, at $1 \times 10^6$ each, were injected into mouse axilla. Tumor growth was assessed once per week by volume monitoring. Mice were euthanized when tumors reached ~1000 mm$^3$ (using L×W×W/2 calculation). For EGFL6-transduced SKOV3 tumor model, EGFL6/GFP co-expressing SKOV3 or GFP-expressing empty-vector SKOV3 were enriched by GFP-gated FACS sorting, and infected into NOD-SCID mouse axilla using $1 \times 10^6$ cells each. Tumor growth was assessed by volume monitoring and fluorescent imaging. At time of euthanasia, tumors were completely resected and weighed to assess terminal tumor burden.

Establishment of HemSC-EGFL6 Tumor Model

HemSCs were transduced with EGFL6-pRSVGFP or control lentivirus, and FACS-sorted based on GFP expression. EGFL6 expression was confirmed by western blot with anti-EGFL6 antibody. SKOV3 whole cells ($1 \times 10^6$) were mixed with EGFL6-expressing HemSCs ($5 \times 10^5$) or equal number of control HemSCs. Mixed cells were injected into axilla of NOD-SCID mice. For EGFL6 antibody therapy, tumors were allowed to engraft for 3 days; then treated with EGFL6 antibody (50 μg/mouse) bi-weekly.

Primary Tumor Processing

Informed consent was obtained from all patients before tissue procurement. All studies were performed with the approval of the Institutional Review Board of the University of Michigan. All tumors were stage III or IV epithelial ovarian or primary peritoneal cancer. Tumors were mechanically dissected into single-cell suspensions and isolated on a ficoll gradient as previously described (see, e.g., Pulaski, H. L., et al. J Transl Med 7, 49 (2009)). For ascites, cell pellets were collected by centrifugation; red cells were lysed using ACK buffer (Lonza, Hopkinton, Mass.), washed, passed through a 40-μm filter, then passed 4 times through a Standard Hub Pipetting needle to isolate single cells (see, e.g., Silva, I. A., et al. Cancer Res (2011)).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

Incorporation by Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

I claim:

1. A method for inhibiting cancer cell proliferation, metastases and/or growth comprising providing a sample comprising cancer cells expressing EGFL6 and exposing said sample to a composition comprising an agent capable of inhibiting EGFL6 function, wherein said agent is an EGFL6 blocking antibody directed against a peptide consisting of the following amino acid sequence: LRAPGTIKDR (SEQ ID NO. 1).

2. The method of claim 1, wherein said cancer cells are selected from the group consisting of cancer stem cells, ovarian cancer cells, ovarian cancer stem cells, and ALDH+ ovarian cancer stem cells.

3. The method of claim 1, wherein said exposing said sample to a composition comprising an agent capable of inhibiting EGFL6 function prevents phosphorylation of one or more of SRC kinase, SHP2 phosphatase.

4. The method of claim 1, wherein said exposing said sample to a composition comprising an agent capable of inhibiting EGFL6 function results in inhibition of proliferation and/or growth of said cancer cells.

5. A composition comprising an antibody directed against an EGFL6 peptide, wherein said antibody is directed against the following amino acid sequence: LRAPGTIKDR (SEQ ID NO. 1).

6. A method for treating a subject suffering from a disorder affected by EGFL6 activity, comprising administering to the subject a composition comprising an agent capable of inhibiting EGFL6 function, wherein said agent is an EGFL6 blocking antibody directed against a peptide consisting of the following amino acid sequence: LRAPGTIKDR (SEQ ID NO. 1).

7. The method of claim 6, wherein said disorder is any type of cancer affected by EGFL6 activity.

8. The method of claim 7, wherein said cancer is ovarian cancer.

9. The method of claim 8, wherein said ovarian cancer comprise ovarian cancer stem cells.

10. The method of claim 9, wherein said ovarian cancer stem cells comprise ALDH+ ovarian cancer stem cells.

11. The method of claim 6, wherein said administration to said subject prevents phosphorylation of SRC kinase and/or prevents phosphorylation of SHP2 phosphatase.

12. The method of claim 8, wherein said administration to said subject results in inhibition of proliferation, metastases and/or growth of said cancer cells.

13. The method of claim 6, wherein said subject is a mammal.

14. The method of claim 6, wherein one or more anti-cancer therapeutic agents are co-administered with said composition comprising an agent capable of inhibiting EGFL6 function.

* * * * *